United States Patent
Rego et al.

(10) Patent No.: US 9,630,203 B2
(45) Date of Patent: Apr. 25, 2017

(54) METHODS AND DEVICES FOR COATING STENTS

(71) Applicant: ABBOTT CARDIOVASCULAR SYSTEMS INC., Santa Clara, CA (US)

(72) Inventors: David Rego, San Diego, CA (US); Kurt Kilchenmann, Rohrbach (CH); Sang joon Park, Waterloo, Ontario (CA); Mark Haight, Cambridge, Ontario (CA); Anthony S. Andreacchi, San Jose, CA (US); Yung-Ming Chen, Cupertino, CA (US); Arnoldo M. Currlin, San Diego, CA (US); Antonio Garcia, San Jose, CA (US); Jason Van Sciver, Los Gatos, CA (US); Thomas David Esbeck, San Diego, CA (US); Bryan D. Glenn, Temecula, CA (US); Patrick A. Tuohy, Temecula, CA (US); Richard Baillargeon, Oceanside, CA (US); Edward P. Garcia, Dublin, CA (US); Steven E. Lehner, Temecula, CA (US); Ian Coulson, Boulder Creek, CA (US)

(73) Assignees: Abbott Cardiovasular Systems Inc., Santa Clara, CA (US); ATS Automation Tooling Systems Inc., Cambridge, Ontario (CA)

( * ) Notice: Subject to any disclaimer, the term of this patent is extended or adjusted under 35 U.S.C. 154(b) by 0 days.

(21) Appl. No.: 14/246,986

(22) Filed: Apr. 7, 2014

(65) Prior Publication Data

US 2014/0299054 A1    Oct. 9, 2014

Related U.S. Application Data

(62) Division of application No. 13/037,075, filed on Feb. 28, 2011, now Pat. No. 8,691,320, which is a division
(Continued)

(51) Int. Cl.
| | | |
|---|---|---|
| B05C 13/02 | (2006.01) | |
| B05B 15/02 | (2006.01) | |
| B05D 1/02 | (2006.01) | |
| B23K 26/402 | (2014.01) | |
| A61F 2/91 | (2013.01) | |
| B05B 13/04 | (2006.01) | |
| B05D 1/00 | (2006.01) | |
| B23K 103/00 | (2006.01) | |

(52) U.S. Cl.
CPC .......... *B05C 13/025* (2013.01); *B05B 15/025* (2013.01); *B05D 1/02* (2013.01); *B23K 26/402* (2013.01); *A61F 2/91* (2013.01); *B05B 13/0442* (2013.01); *B05D 1/002* (2013.01); *B23K 2203/42* (2015.10); *Y10T 137/313* (2015.04)

(58) Field of Classification Search
CPC ....................................................... B29C 70/44
USPC ........................................................... 264/57
See application file for complete search history.

(56) References Cited

U.S. PATENT DOCUMENTS 4,562,088 A    12/1985 Navarro
6,592,796 B2 *  7/2003 Hill et al. ..................... 264/257
(Continued)

*Primary Examiner* — Dah-Wei D Yuan
*Assistant Examiner* — Andrew Bowman
(74) *Attorney, Agent, or Firm* — Squire Patton Boggs (US) LLP

(57) ABSTRACT

Various embodiments of methods and devices for coating stents are described herein.

8 Claims, 19 Drawing Sheets

Related U.S. Application Data of application No. 11/764,006, filed on Jun. 15, 2007, now Pat. No. 7,897,195.

(56) References Cited

U.S. PATENT DOCUMENTS

| | | |
|---|---|---|
| 7,718,213 B1 | 5/2010 | Scheer |
| 2002/0041899 A1 | 4/2002 | Chudzik et al. |
| 2002/0124798 A1 | 9/2002 | Kitano et al. |
| 2004/0187775 A1 | 9/2004 | Kerrigan |

* cited by examiner

METHODS AND DEVICES FOR COATING STENTS

CROSS-REFERENCE TO RELATED APPLICATIONS

This application is a divisional of application Ser. No. 13/037,075, filed Feb. 28, 2011, now U.S. Pat. No. 8,691,320, which is a divisional of application Ser. No. 11/764,006, filed Jun. 15, 2007, now U.S. Pat. No. 7,897,195, both of which applications are incorporated herein by reference.

BACKGROUND OF THE INVENTION

Field of the Invention

This invention relates to methods and devices for coating stents.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site. Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of a stent with an active agent or an active agent and a polymeric carrier. Those of ordinary skill in the art fabricate coatings by applying a polymer, or a blend of polymers, to the stent using well-known techniques. Such a coating composition may include a polymer solution and an active agent dispersed in the solution. The composition may be applied to the stent by immersing the stent in the composition or by spraying the composition onto the stent using various kinds of apparatus'. The solvent then evaporates, leaving on the stent surfaces a polymer coating impregnated with the drug or active agent.

The accuracy of drug loading, the uniformity of the drug distribution, stent coating quality, and coating material selection are critical factors in making the drug eluting stent. Having a robust and cost effective drug eluting stent manufacturing process to enable good coating quality, high throughput, high yield, low machine down time is an important goal for coated stent manufacturers.

SUMMARY OF THE INVENTION

Various embodiments of the present invention include a device for coating a stent comprising: a first support for supporting a first stent, the first support being coupled to a movable member; and a second support for supporting a second stent, the second support being coupled to the movable member, the movable member configured to position one of the supports in a spraying zone and the other support in a drying zone, wherein the stent in the spraying zone can be spray coated while the stent in the drying zone is dried.

Further embodiments of the present invention include a method of coating a stent comprising: applying a coating material to a first stent on a first support positioned in a spraying zone of a device; and drying a second stent supported on a second support while applying the coating material to the first stent, the second support positioned in a drying zone of the device, wherein the device comprises a movable member configured to position one of the supports in a spraying zone and the other support in a drying zone.

Additional embodiments of the present invention include a device for coating a stent comprising: a spray nozzle disposed within a spraying zone of a device; and a first support for supporting a first stent and a second support for supporting a second stent, the first support and the second support being coupled to a member capable of positioning one of the supports in the spraying zone below the spray nozzle to receive coating material from the spray nozzle and the other support in a drying zone, wherein the spray nozzle is movable with respect to the support in the spraying zone while the stent in the drying zone is drying, the spray nozzle being movable so that the support does not receive coating material.

Other embodiments of the present invention include a method of coating a stent comprising: applying a coating material with a spray nozzle positioned over a first stent supported on a first support positioned in a spraying zone; drying a second stent supported on a second support while applying the coating material to the first stent, the second support positioned in a drying zone; and shifting the spray nozzle away from the first support to prevent further application of coating material on the first stent while the second stent is drying, the spray nozzle continuing to spray after shifting.

Certain embodiments of the present invention include a stent coating device comprising: a rotatable support for supporting a stent, the support capable of rotating the stent about a cylindrical axis of the support; and a gripping mechanism positioned below the support capable of actuating upwards to apply a force to an outside surface of the stent to prevent rotation of the stent with respect to the support.

Further embodiments of the present invention include a method of coating a stent comprising: applying a coating material to a stent mounted on a rotatable support; applying a force to an outside surface of the stent with a gripping mechanism; and rotating the support while the force is applied to the outside surface of the stent, wherein the force prevents rotation of the stent with respect to the support.

Certain additional embodiments of the present invention include a device for coating a stent comprising: a spray nozzle for applying a coating material to a stent when the spray nozzle is positioned above the stent; a container for a solvent for cleaning the spray nozzle; and a movable support member coupled to the spray nozzle to move the spray nozzle from a position above the stent to a position above the container to allow cleaning of the spray nozzle with the solvent.

Additional embodiments of the present invention include a method of coating a stent comprising: spraying a coating material from a spray nozzle to coat a stent; moving the spray nozzle from a spraying position above the stent with a movable support member coupled to the spray nozzle to a position above a container to allow cleaning of the nozzle with a solvent within the container; and contacting the spray nozzle with the solvent within the container.

Certain other embodiments of the present invention include a method for coating a stent comprising: feeding a gas and a liquid into a spray nozzle for coating a stent, the spray nozzle producing a spray plume from the gas and liquid fed to the nozzle; monitoring the gas flow properties and the liquid flow properties prior to feeding the gas and liquid into the spray nozzle during the coating; and adjusting the gas flow properties and liquid flow properties to obtain selected flow properties of gas and liquid into the spray nozzle, wherein the adjustment is based on the monitored gas and liquid flow properties.

Other embodiments of the present invention include a device for coating a stent comprising: a spray nozzle for spraying a stent, the spray nozzle adapted to spray a spray plume produced from liquid and gas fed to the nozzle; a gas flow control system for monitoring and controlling the flow of gas into the nozzle during the spraying; and a liquid flow control system for monitoring and controlling the flow of liquid into the nozzle during the spraying.

Further embodiments of the present invention include a support assembly for supporting a stent during coating comprising: a first support element with a proximal end disposed within a rotatable spindle; a support wire extending from a distal end of the first support element, the proximal end of the support wire coupled to the distal end of the first support element; and a clamping element supporting a distal end of the support wire, wherein the proximal end and the distal end of the of the support wire are positioned so that the support wire rotates concentrically with the first support element when the first support element is rotated by the rotatable spindle.

Certain other embodiments of the present invention include a method of coating a stent comprising: calibrating a spray nozzle for coating a stent so that a spray plume from the nozzle has selected properties; mounting the calibrated spray nozzle in a spray device, wherein a spray plume from the mounted nozzle has the selected properties; and spray coating a stent using the mounted spray nozzle.

Additional embodiments of the present invention include a device for coating a stent comprising: a spray nozzle for applying a coating material; a drying nozzle for drying a coated stent; and a first stent support and a second stent support, the first stent support and the second stent support coupled to a movable member, the movable member capable of positioning one of the stent supports for coating with the spray nozzle and the other stent support for drying with the drying nozzle.

DETAILED DESCRIPTION OF THE INVENTION

Embodiments of the present invention relate to coating implantable medical devices such as stents. In particular, the embodiments of the present invention relate to aspects of methods and devices for spray coating and drying stents.

More generally, embodiments of the present invention may also be used in coating devices including, but not limited to, self-expandable stents, balloon-expandable stents, stent-grafts, vascular grafts, cerebrospinal fluid shunts, pacemaker leads, closure devices for patent foramen ovale, and synthetic heart valves.

In particular, a stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

In other embodiments, a metallic or polymeric filament or wire may also be coiled to form the stent. Filaments of polymer may be extruded or melt spun. These filaments can then be cut, formed into ring elements, welded closed, corrugated to form crowns, and then the crowns welded together by heat or solvent to form the stent.

Figure 1:
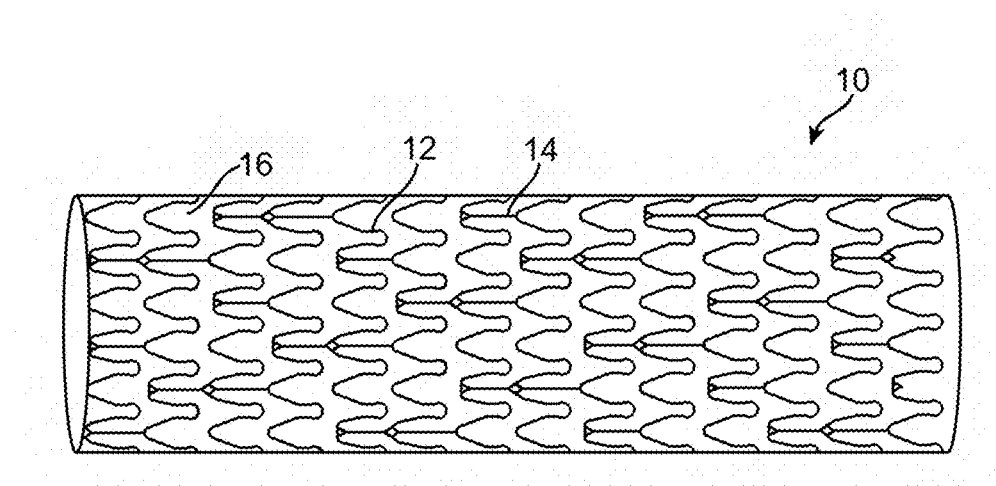
FIG. 1 depicts a three-dimensional view of a cylindrically-shaped stent.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

The cross-section of the struts in stent 10 may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

Coating a Stent

As indicated above, a medicated coating on a stent may be fabricated by spraying a coating composition including polymer and drug on the stent. Spray coating a stent typically involves mounting or disposing a stent on a support, followed by spraying a coating material from a nozzle onto the mounted stent.

A spray apparatus, such as EFD 780S spray device with VALVEMATE 7040 control system (manufactured by EFD Inc., East Providence, R.I.) can be used to apply a composition to a stent. An EFD 780S spray device is an air-assisted external mixing atomizer. The composition is atomized into small droplets by air and uniformly applied to the stent surfaces. Other types of coating applicators, including air-assisted internal mixing atomizers (such as IVEK SonicAir nozzle), ultrasonic applicators (such as Accu-Mist nozzle or MicroMist nozzle from SonoTek Co. in Milton, N.Y.), or drop dispensing device can also be used for the application of the composition.

To facilitate uniform and complete coverage of the stent during the application of the composition, the stent can be rotated about the stent's central longitudinal axis. Rotation of the stent can be from about 0.1 rpm to about 300 rpm, more narrowly from about 30 rpm to about 200 rpm. By way of example, the stent can rotate at about 150 rpm. The stent can also be moved in a linear direction along the same axis. The stent can be moved at about 1 mm/second to about 30 mm/second, for example about 6 mm/second, or for a minimum of at least two passes (i.e., back and forth past the spray nozzle). In other applications, the spray nozzle can be devised to translate over the stent. The stent is rotated at a desired speed underneath the nozzle.

A nozzle can deposit coating material onto a stent in the form of fine droplets. An atomization pressure of a sprayer can be maintained at a range of about 5 psi to about 30 psi. The droplet size depends on factors such as viscosity of the solution, surface tension of the solvent, solution feed rate, and atomization pressure. The flow rate of the composition from the spray nozzle can be from about 0.01 mg/second to about 1.0 mg/second, for example about 0.1 mg/second. Only a small percentage of the composition that is delivered from the spray nozzle is ultimately deposited on the stent depending on the transfer efficiency of the spray setup. By way of example, when a composition is sprayed to deliver about 1 mg of solids, only about 100 micrograms or about 10% of the solids sprayed will likely be deposited on the stent. The solid percent in the composition typically can range from 0.1 wt % to 15 wt %, for example about 5 wt %.

To reduce or eliminate coating defects in coated stents, excessive solvent is removed from applied coating material through an in-process drying cycle. Excessive application of the polymer or excessive solvent left in the coating can cause coating defects such as pool web (excessive material accumulated between stent struts) due to the lack of good wettability of the coating droplets over a stent with a tight geometry.

To avoid excessive application of coating material, the coating process can involve multiple repetitions of spraying forming a plurality of layers. A repetition can involve a single pass or multiple passes of moving a spray nozzle (or moving the stent), a pass being from one end (e.g., proximal end) to the other end (e.g., distal end) of a stent. Each repetition can be, for example, about 0.5 second to about 20 seconds, for example about 10 seconds in duration. The amount of dry coating applied by each repetition can be about 1 microgram/cm$^2$ (of stent surface) to about 75 micrograms/cm$^2$, for example, less than about 20 micrograms/cm$^2$.

As indicated above, the coating composition can include a polymer and a drug dissolved in a solvent. Each repetition can be followed by in-process drying involving removal of a significant amount of the solvent(s). In an embodiment, there may be less than 5%, 3%, or more narrowly, less than 1% of solvent remaining in the coating after in-process drying between repetitions. When the coating process is completed, all or substantially all of the solvent may be removed from the coating material on the stent. Any suitable number of repetitions of applying the composition followed by removing the solvent(s) can be performed to form a coating of a desired thickness or weight. Excessive application of the polymer can, however, cause coating defects.

A stent coated with coating material can be dried by allowing the solvent to evaporate at room or ambient temperature. Depending on the volatility of the particular solvent employed, the solvent can evaporate essentially upon contact with the stent. Alternatively, the solvent can be removed by subjecting the coated stent to various drying processes. Drying time can be decreased to increase manufacturing throughput by heating the coated stent. For example, removal of the solvent can be induced by baking the stent in an oven at a mild temperature (e.g., 60° C.) for a suitable duration of time (e.g., 2-4 hours) or by the application of warm air. There can be some residual solvent left in the coating after the in-process drying depending on the solvent used and in-process drying time. The higher the boiling point of the solvent, the harder it is to remove solvent in the in-process drying process. The coated stent is typically dried in an oven as the final drying step when the multiple deposition stages are completed to remove residual solvent. The residual solvent can have harmful biological effects and plasticizing effects which can alter the release rate and coating properties. The energy source of the oven can range from a conventional oven to an infrared oven or UV.

Evaporation of the solvent(s) can be induced by application of a warm gas between each repetition which can prevent coating defects and minimize interaction between the active agent and the solvent. The stent may be positioned below a nozzle blowing a warm gas. A warm gas may be particularly suitable for embodiments in which the solvent employed in the coating composition is of a low volatility (e.g., dimethylsulfoxide (DMSO), dimethylformamide (DMF), and dimethylacetamide (DMAC)). The temperature of the warm gas can be from about 25° C. to about 200° C., more narrowly from about 40° C. to about 90° C. By way of example, warm gas applications can be performed at a temperature of about 60° C., at a flow speed of about 5,000 feet/minute, and for about 10 seconds.

The gas can be directed onto the stent following a curing period of about 3 seconds to about 60 seconds, more narrowly for about 10 seconds to about 20 seconds, so as to allow the residual solvent(s) to be removed to form a coating. The curing period is particularly short if the coating composition contains a volatile solvent since such solvents are typically removed quickly. As used herein "volatile solvent" means a solvent that has a vapor pressure greater than 17.54 Torr at ambient temperature, and "non-volatile solvent" means a solvent that has a vapor pressure less than or equal to 17.54 Torr at ambient temperature.

Any suitable gas can be employed, examples of which include air, argon, or nitrogen. The flow rate of the warm gas can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm gas can be applied for about 3 seconds to about 60 seconds. By way of example, warm air applications can be performed at a temperature of about 50° C., at a flow rate of about 40 CFM, and for about 10 seconds.

Figure 2:
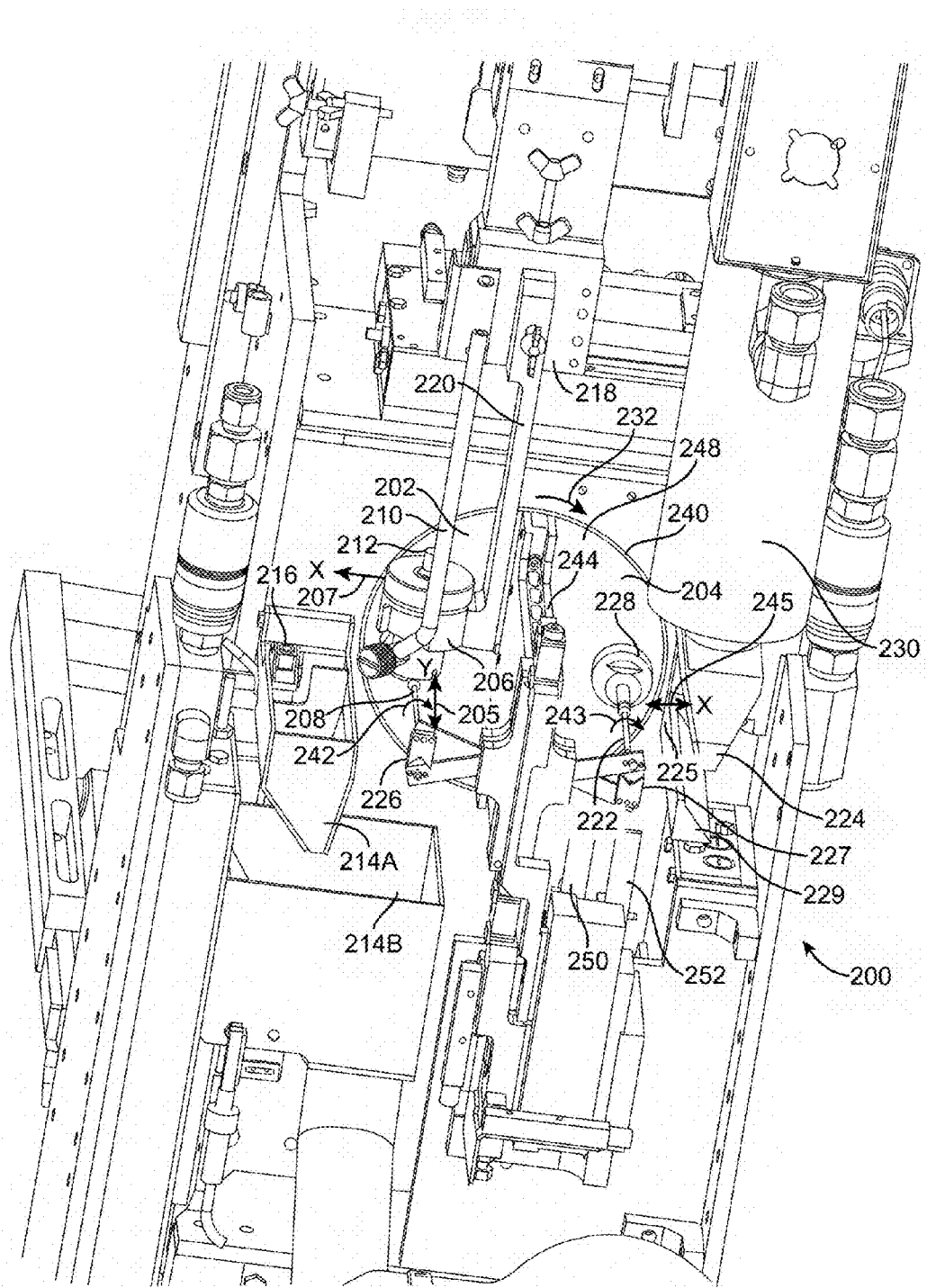
FIG. 2 depicts an exemplary stent coating and drying device.

Embodiments of the present invention may be illustrated by the exemplary spray coating device 200 depicted in FIG. 2, which shows a front view. Device 200 is configured to process two stents simultaneously. However, device 200 can process only one stent if desired. Device 200 has a spraying zone 202 and a drying zone 204, which enable coating of one stent and drying of another stent simultaneously. Stent support assemblies 208 and 222 can be moved between spraying zone 202 and drying zone 204 via a rotating drum to allow simultaneous spraying of a stent on one stent support assembly and drying of another stent on another stent support assembly.

Spraying zone 202 has a spray nozzle 206 that is mounted above movable stent support assembly 208. Stent support assembly 208 is inserted into a spindle which is connected to a gear system that is powered by a motor (not shown) which provides rotational motion to the stent support assembly 208, as depicted by an arrow 242, during the coating process. Hose 210 feeds gas to spray nozzle 206 and liquid coating material is fed to spray nozzle 206 via port 212. A tubing or line (not shown) can connect port 212 to a liquid coating material source. Spray nozzle 206 is translatable along a y-direction, as shown by double-headed arrow 205, along the axis of stent support assembly 208. Spray nozzle 206 is also movable along an x-direction as shown by an arrow 207.

Spraying zone 202 includes upper funnel 214A and lower funnel 214B. Lower funnel 214B is connected to an evacuation system that creates a vacuum at funnel 214A and 214B to collect excess coating material generated from the over-spray. The evacuation system can be on during all or part of the coating process. A wetcap device 216, described in more detail below, adjacent to upper funnel 214A is for cleaning the tip of spray nozzle 206.

Spray nozzle 206 is dwelled in a nozzle holder 220 which is attached to a mounting bracket block 218. Mounting bracket block 218 is coupled to a linear slide that can control movement of nozzle holder 220 and spray nozzle 206 back and forth in the x-direction during the application of the coating material over the stent. Mounting bracket block 218 is also coupled to a sliding stage to enable nozzle holder 220 along with spray nozzle 206 to side shift back and forth in the y-direction to a position over upper funnel 214A after a spray cycle is complete. The side-shifting of nozzle holder 220 along with spray nozzle 206 clears the path in the spray zone to allow the drum to rotate to advance the stent at the drying zone 204 to the spraying zone 202 to receive coating material. The side shift motion clears the path in the spray zone to allow the drum to rotate, advancing the stent at the drying zone to the spray zone to receive to more coating material.

Drying zone 204 includes a drying nozzle 224 that can be positioned over a movable stent support assembly 222 for supporting a coated stent during drying. Stent support assembly 222 is inserted into a spindle which is connected to a gear system that is powered by a motor (not shown) which provides rotational motion to the stent support assembly 222, as depicted by an arrow 243, during the drying process. In some embodiments, the same motor provides rotational motion to stent support assemblies 208 and 222. Drying nozzle 224 includes an electrical heater 230 to generate heated air for drying nozzle 224. Drying nozzle 224 is movable and can shift in an x-direction, as shown by a double-headed arrow 245, from its position shown in FIG. 2 to a drying position over stent support assembly 222. Drying nozzle 224 can be positioned above stent support assembly 222 so that it can dry a stent coated in spraying zone 202 by blowing warm gas over a freshly coated stent. Stent grippers 250 and 252 for clocking a stent, as described in detail below, are disposed below stent support assembly 222.

Movement of mounting bracket 220, and thus, nozzle 206, is accomplished by motors (not shown). Shifting of drying nozzle 224 is performed by motors (not shown). The motors can be controlled by a controller that has pre-programmed instructions on the movement of nozzles 206 and 224.

The side shift of drying nozzle 224 and spray nozzle 206 may be accomplished with pneumatic slides or motor driven linear slides. The side-shift of the drying nozzle allows the indexing drum to rotate, but also accommodates differences in the drying time and the spraying time. The side-shift of drying nozzle 224 results in a deflection of the drying air away from the stent to prevent over-drying while the other stent is finishing its spray cycle. Thus, the spray cycle and dry cycle are not limited to the same duration for process flexibility.

Stent support assemblies 208 and 222 are supported at their distal ends by clamps 226 and 227, respectively. The proximal end of stent support assembly 222 is shown to be supported by a spindle or end cap 228. The distal end of stent support assembly 208 is supported in the same manner, but is hidden by spray nozzle 206. End cap 228 is mounted or coupled on a rotatable drum 240 which rotates as shown by arrow 232. Rotatable drum 240 can rotate to reverse the position of stent support assemblies 208 and 222 so that stent support assembly 208 is in drying zone 204 and stent support assembly 222 is in the spray zone 202.

The scissor-type end supports facilitate automatic loading/unloading of parts to the spindles. Since the supports are mounted to a baffle 244, ends of the mandrels are supported during the indexing of the drum. This prevents oscillation of the core wires with collets which could damage the coating. Such oscillation would limit the acceleration/deceleration of indexing of the drum.

In some embodiments, device 200 can be used as part of an automated process. Robotic arms (not shown) can position a shaft of stent support assemblies 208 and 222 that include an uncoated stent within holes in endcaps or spindles. After coating is completed, the robotic arm can remove the stent support assemblies from the endcaps or spindles. Gripping collets inside the spindles can be opened and closed automatically to allow automated loading/unloading of parts.

Spray zone 202 and drying zone 204 are separated by baffle 244 which is mounted on a back plate 248 of rotatable drum 240. Baffle 244 is configured to reduce or eliminate heat and mass transfer between spray zone 202 and drying zone 204. In particular, baffle 244 reduces or prevents coating material sprayed from nozzle 206 from contacting a stent that is being dried in drying zone 202. Additionally, baffle 244 acts as a thermal barrier that reduces or prevents conductive or convective heat transfer between spray zone 202 and drying zone 204. In particular, baffle 244 reduces or prevents conductive heat transfer to spraying zone 202 due to heated gas from drying nozzle 224. Baffle 244 also blocks air currents that may carry coating material to drying zone 204 or heated air to spraying zone 202.

Figure 3:
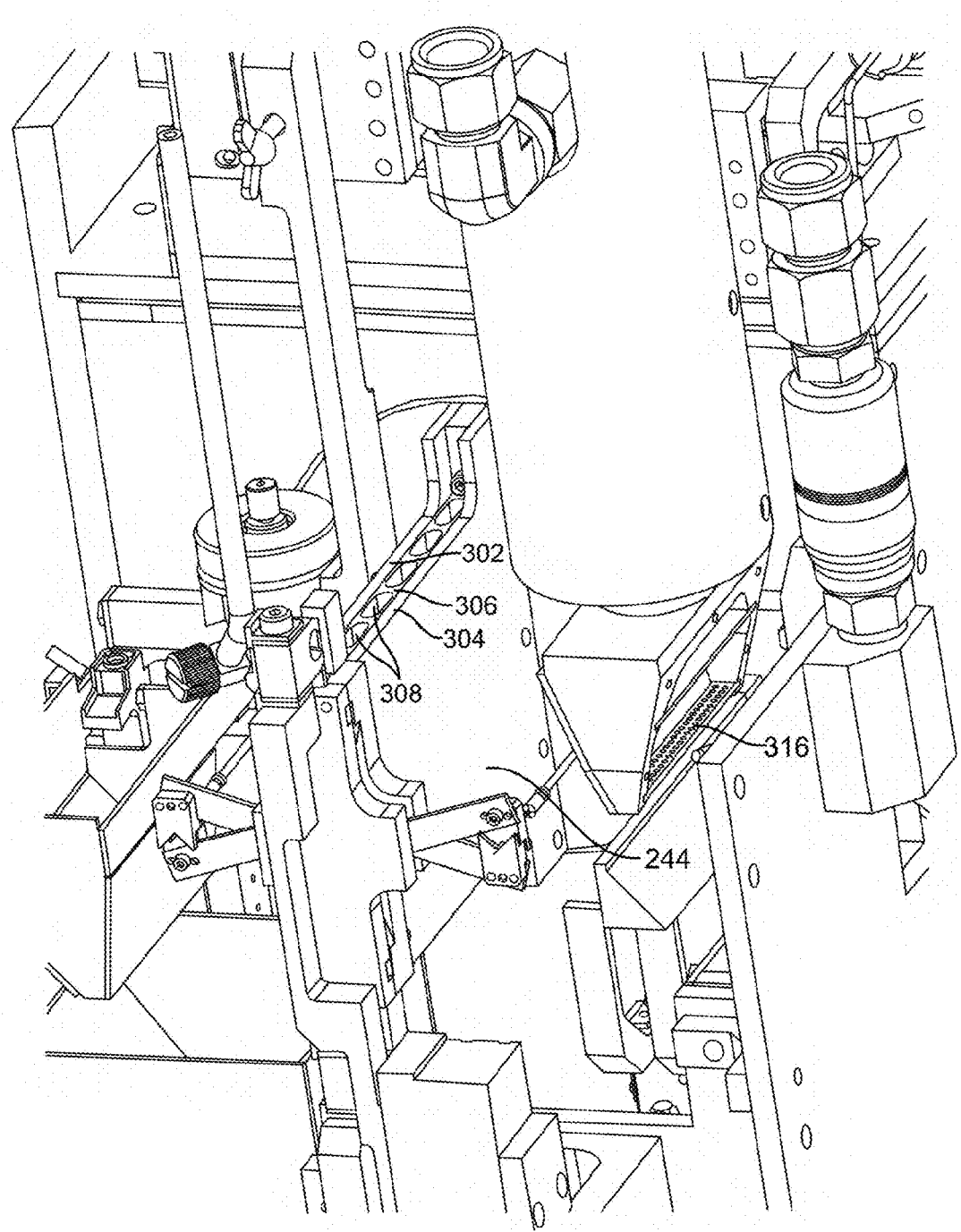
FIG. 3 depicts a close-up view of a baffle separating a spraying zone and a drying zone in the device depicted in FIG. 1.

Baffle 244 can be fabricated of materials that provide thermal insulation between spraying zone 202 and drying zone 204. In addition, such materials should also maintain thermal and mechanical properties during the spraying and coating process. For example, the materials should be insoluble in the solvent(s) used in the coating material and should be resistant to significant changes in properties caused by the heat from drying nozzle 224. For example, baffle 244 can be fabricated at least in part of a polymeric or plastic material. A close-up view of baffle 244 is provided in FIG. 3. Baffle 244 is a composite structure having two outer polymer plates 302 and 304 that provide thermal insulation. Baffle 244 has an inner metallic support 306 to provide a rigid structural support to baffle 246. Metallic layer 306 has channels or voids 308 to reduce the heat conduction through baffle 244 and which also provides the required space to accommodate an end support mechanism to the stent support assemblies to improve the alignment of the assemblies to the nozzles as illustrated in FIG. 11C. In an exemplary embodiment, baffle 244 has outer layers fabricated from polyetheretherketone (PEEK) and an inner layer of stainless steel. The structure of baffle 244 is not limited to that depicted in FIG. 3.

As indicated above, it is desirable to coat stents with multiple spray/dry cycles Device 200 is designed to allow spraying of stent in spray zone 202 while a coating layer previously applied at spray zone 202 is dried at drying zone 204. Simultaneous spraying and drying reduces or eliminates idle time of sequential spraying and drying operation, thus increasing the throughput of a coating operation.

Specifically, a layer of coating material is applied to a first stent mounted on stent support assembly 208 by spray nozzle 206. At the same time, a second stent mounted on stent support assembly 222 with coating material already applied in spray zone 202 is dried by drying nozzle 224. When both the spray coating on the first stent and drying of the second stent are completed, rotatable drum 240 rotates and positions the second stent (dried) at spray zone 202 and the first stent (freshly coated) at drying zone 204. The first stent may then be dried at drying zone 204 and a layer of coating material can be applied to the second stent at spray zone 202. The spraying and drying can be repeated a selected number of times necessary to obtain a desired coating mass on each of the stents. Rotatable drum 240 can rotate clockwise or counterclockwise to change the position of the first stent and second stent between spray zone 202 and drying zone 204. The motion of rotatable drum 240 can be controlled by a belt driven gear assembly (not shown) which is powered by a motor (not shown). Stent support assembly 208 and stent support assembly 222 are rotated in each spraying and drying cycle. As shown by arrow 232, the first stent is rotated to spray zone 202 and the second stent is rotated to drying zone 204, and after the spraying/drying cycle is complete the first stent is rotated back to drying zone 204 for drying the stent and the second stent is rotated to spray zone 202 to receive coating material.

To allow rotation of rotatable drum 240 when both the spray coating of a first stent and drying of a second stent are completed, spray nozzle 206 shifts away from stent support assembly 208. In addition, drying nozzle 224 can also shifts away from stent support assembly 222 to allow rotation of rotatable drum 240.

Figure 4:
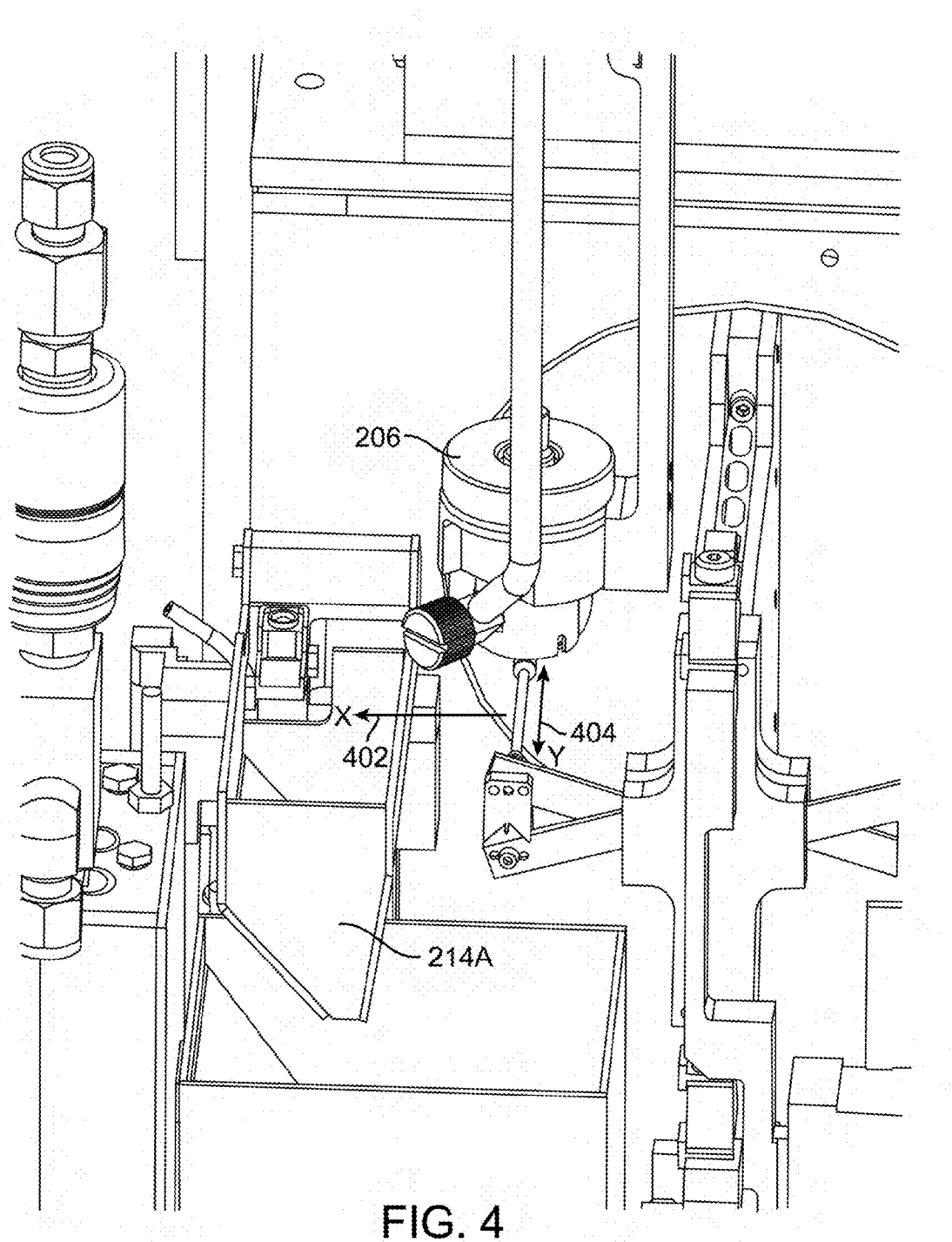
FIG. 4 depicts a close-up view of a spray zone of the device depicted in FIG. 1.

A close-up view of spray zone 202 is shown in FIG. 4. Spray nozzle 206 can shift in an x-direction to a position over upper funnel 214A, as shown by an arrow 402. As indicated above, spray nozzle 206 translates linearly along the y-axis, as shown by an arrow 404, of stent support assembly 208 during application of coating material to a stent mounted on stent support assembly 208. Spray nozzle 206 can side shift in the x-direction to be positioned over upper funnel 214A after the spray cycle is complete and spray nozzle 206 can rest at any position along the y-axis over funnel 214A to await the next spray cycle. Spray nozzle 206 can continue spraying or turn off while it is waiting, or it can advance to the wetcap device 216 for wet-capping to clean the nozzle tip.

Figure 5A:
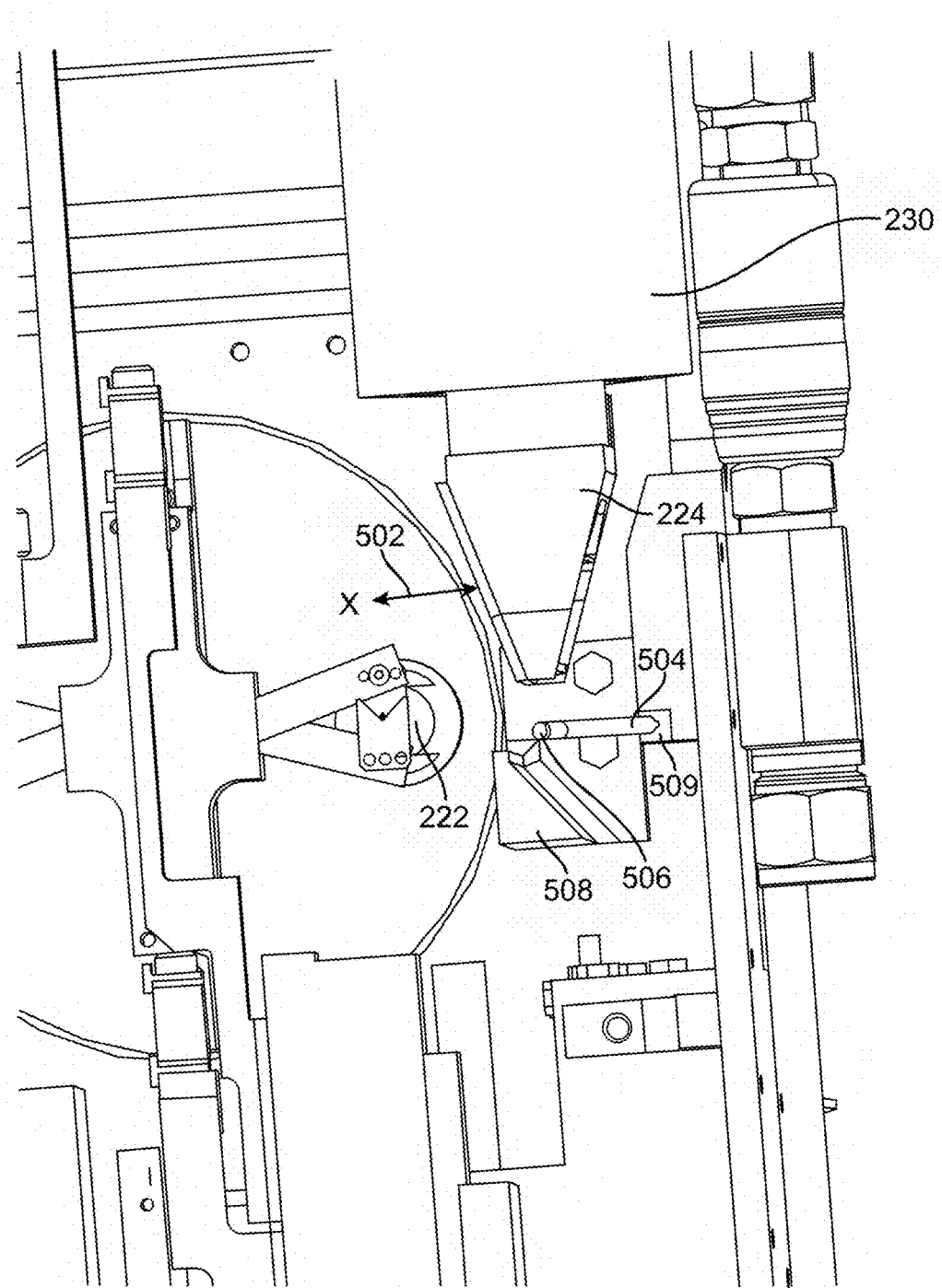
FIGS. 5A-B depict a close-up view of a drying zone of the device depicted in FIG. 1.
Figure 5B:
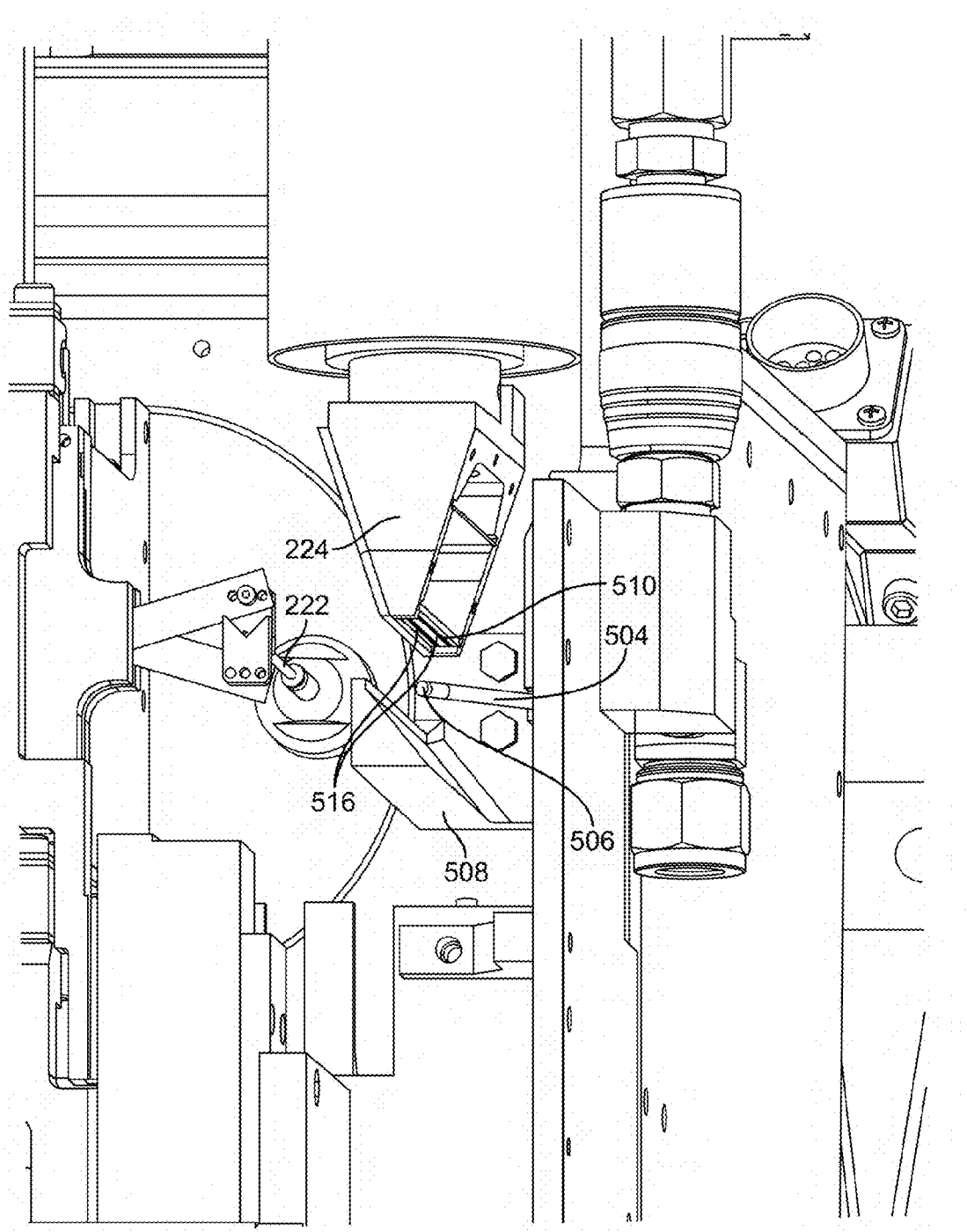

FIGS. 5A-B depict a close-up view of drying zone 204. Drying nozzle 224 is shown shifted away from a position above stent support assembly 222, as shown by an arrow 502, to a position as shown. A temperature probe 504 with a sensing zone 506 at its tip extends outward toward drying nozzle 224. Temperature probe 504 monitors the temperature of warm gas stream exiting from drying nozzle 224. Temperature probe 504 is coupled to a housing 509. The housing 509 and drying nozzle 224 are both attached to a linear stage which enables and maintains the alignment of drying nozzle 224 to temperature probe 504. Temperature probe 504 and drying nozzle 224 move back and forth along the x-direction so that temperature probe 504 remains a fixed distance from drying nozzle 224 and can continue to monitor the temperature of the warm gas stream.

FIG. 5B shows a slotted opening 510 through which warm gas passes for drying a coated stent mounted on stent support assembly 222. A deflector shield 508 is positioned below drying nozzle 224 in its right-most shifted position. Deflector shield 508 deflects the warm gas stream exiting drying nozzle 224 to the downstream evacuation when drying nozzle 224 is shifted away from stent support assembly 222 when the drying cycle is complete. Perforated plates or screens 516 can be incorporated into drying nozzle 224 to improve the mixing of the hot gas exiting from the heating element (not shown) located at the upper portion of drying nozzle 224 to provide an air stream with a uniform temperature distribution.

The time for drying a stent with drying nozzle 224 can be different from the time for spraying a layer of coating material on a stent with spray nozzle 206. In some embodiments, spraying nozzle 206 can finish a coating layer on a stent mounted on a stent support assembly prior to a stent mounted on a stent support assembly is finished drying. In one embodiment, the flow of coating material from spray nozzle 206 can be stopped after completing the deposition of a layer on a first stent in spraying zone 202. The spraying and drying can be started again after rotatable drum 240 has rotated and positioned the stent from the drying zone in spraying zone 202 and the freshly coated stent in drying zone 204.

A potential disadvantage of stopping the flow of coating material is nozzle fouling which refers to residual coating material in the nozzle drying up and reducing or preventing flow of coating material through the nozzle. Nozzle fouling can degrade the nozzle performance and it can reduce the coating weight consistency and coating quality. In an alternative embodiment, spray nozzle 206 can continue to spray coating material even after completing deposition of a coating layer on a stent in spraying zone 204 to minimize nozzle fouling. Spray nozzle 206 can shift in the x-direction to a position away from the coated stent so that no additional coating material is applied to the stent. Spray nozzle 206 can be positioned adjacent to or above funnel 214 after completing deposition to prevent further deposition of coating material on the stent. The evacuation system (not shown) creates a vacuum at upper funnel 214A and removes all or a substantial portion of the coating material that continues to be sprayed from spray nozzle 206.

Figure 6:
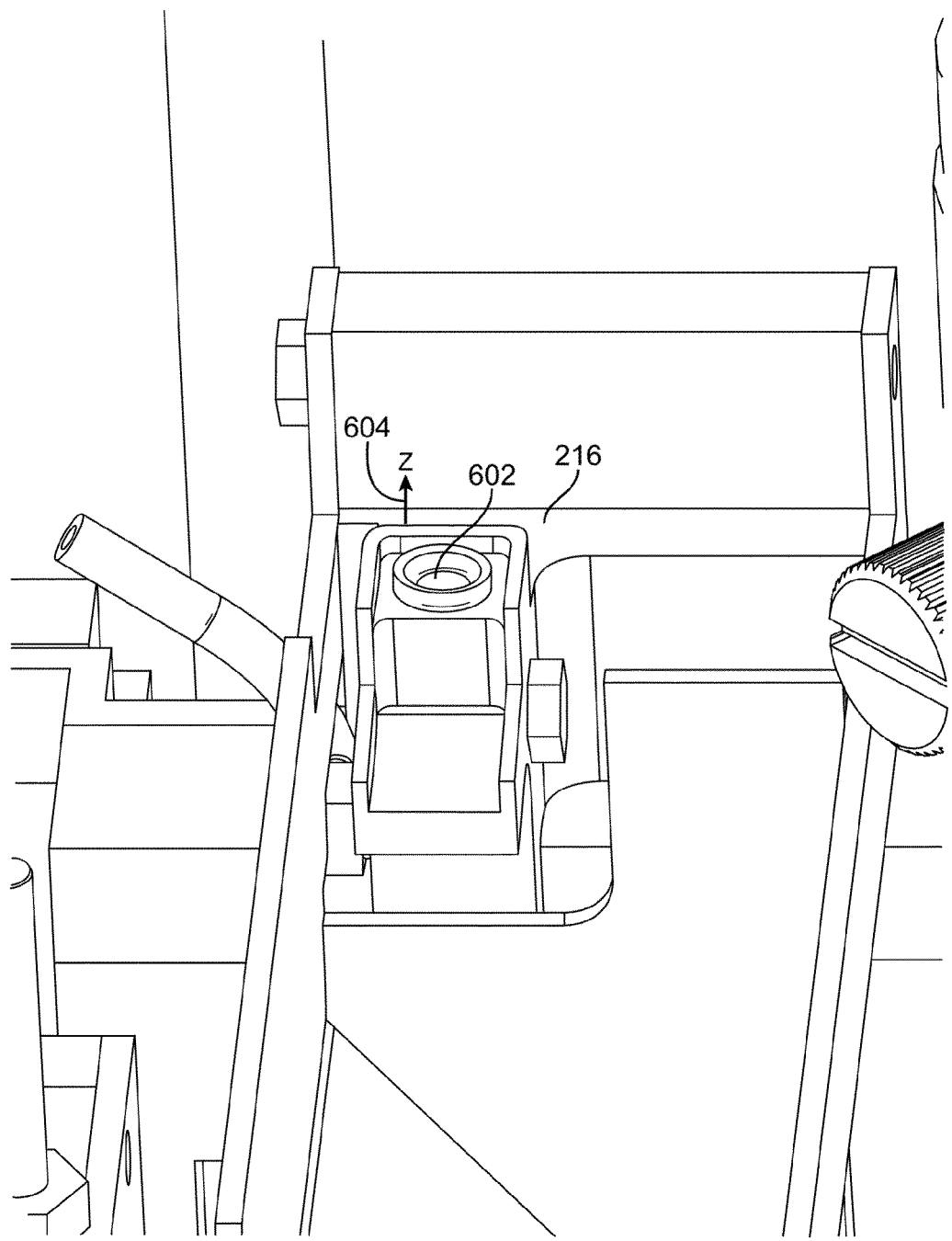
FIG. 6 depicts a close-up view of a cap fixture.

As described above, a wetcap device 216 shown in FIG. 2 is provided for cleaning the tip of spray nozzle 206. Wetcap device 216 can remove coating material that may have accumulated at the tip of spray nozzle 206 by using a solvent that can soften or dissolve the build-up of coating material at the nozzle tip. FIG. 6 depicts a close-up view of wetcap device 216. Wetcap device 216 has an opening or solvent well 602 to allow the solvent, supplied from an external solvent supply system (not shown) to form a meniscus to allow the material build up at the nozzle tip to be dissolved or to be softened. In one embodiment, the solvent is the same as the solvent used in the coating material. To clean the tip of spray nozzle 206 with wetcap device 216, spray nozzle 206 is shifted in the x-direction, y-direction, or a combination of both so that it is positioned above opening 602 of cap fixture 216. Cap fixture 216 is configured to move upward in the z-direction, as shown by an arrow 604. Cap fixture 216 is moved upward an amount sufficient for the tip of spray nozzle 206 is immersed in solvent well 602 in the chamber.

Figure 7:
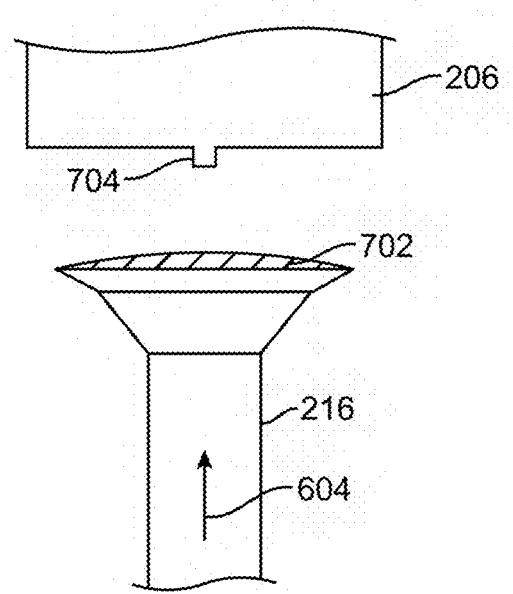
FIG. 7 shows a schematic side view of spray nozzle positioned above the cap fixture of FIG. 6.

FIG. 7 shows a schematic side view of spray nozzle 206 positioned above cap fixture 216 that contains a solvent 702. As shown by arrow 604, cap fixture 216 can shift upward so that tip 704 of spray nozzle 206 is immersed in solvent 702. Nozzle tip 604 remains immersed in the solvent a sufficient period of time to remove coating material from the tip. After cleaning of nozzle tip 704, cap fixture 216 is lowered and spray nozzle 206 is shifted back into a position for spraying a stent.

Nozzle tip 704 can be cleaned with cap fixture 216 at any time there is a lapse in spraying, i.e., between applications of a coating layer or a repetition. Specifically, nozzle tip 704 can be cleaned at cap fixture 216 to prior and/or during reversing the positions of stent support assemblies 208 and 222 with rotation drum 240. Nozzle tip 704 can be cleaned after every coating layer/repetition or at any frequency of coating layers. In one embodiment, nozzle tip 704 is cleaned when the coating of the two stents is completed. Nozzle tip 704 can be cleaned while the coated stents are removed from stent support assemblies 208 and 222 and uncoated stents are mounted on the stent support assemblies.

It is important for the solvent well 602 in cap fixture 216 to be filled with enough solvent enough so that nozzle tip 704 is immersed in the solvent when cap fixture 216 shifts upward. The level of solvent in cap fixture 216 can change with time due to evaporation of the solvent. It may be necessary to continuously or periodically monitor the level of solvent in cap fixture 216 to maintain the level of solvent so the nozzle tip is immersed when cap fixture 216 is raised.

Figure 8A:
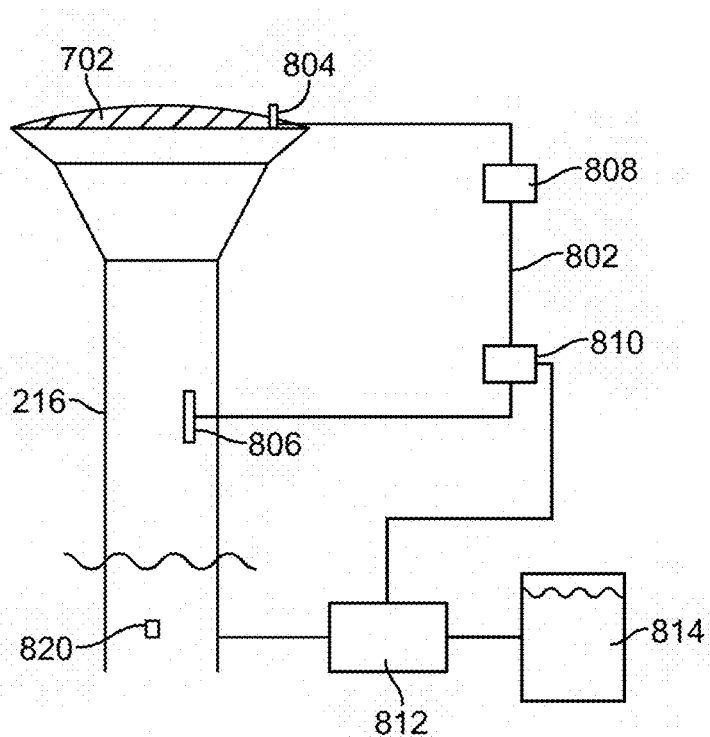
FIGS. 8A-B depict embodiments for controlling the level of solvent in a cap fixture.
Figure 8B:
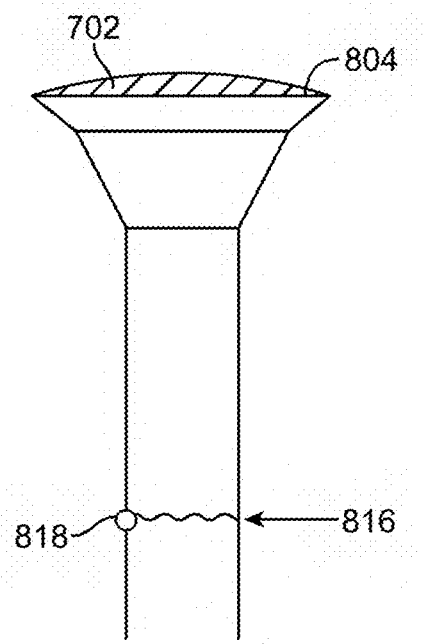

Various methods can be used to control the level of solvent in cap fixture 216 so that nozzle tip 704 is immersed when cap fixture 216 is shifted upwards. Exemplary embodiments are depicted in FIGS. 8A-B. The embodiment in FIG. 8A includes a conductivity loop 802. Conductivity loop 802 has at one end an electrical lead 804 positioned at a desired level of solvent in cap fixture 216. At another end of conductivity loop 802, an electrical lead 806 is positioned in cap fixture 216 below electrical lead 804. An electrical current is passed through conductivity loop 802 from current source 808. A resistometer 810 monitors changes in resistance in conductivity loop 802. Conductivity loop 802 remains closed as long as the level of solvent remains at or above the position of electrical lead 804. When the level of solvent in cap fixture 216 goes below the position of electrical lead 804, resistometer 810 detects an open loop due to an increase in resistance. Resistometer 810 is in communication with a pump 812. Pump 812 can receive a signal from resistometer 810 which causes pumping of solvent from a solvent reservoir 814 into cap fixture 216 until the level of solvent in cap fixture 216 is restored to the level of electrical lead 804. Pump 812 can be configured to stop pumping solvent when it receives a signal from resistometer 810 of a decrease in resistance due to closing of conductivity loop 802.

In a similar manner, a conductivity loop can be between electrical lead 804 and nozzle tip 704. The continuity of this conductivity loop detects whether the tip of the nozzle is in the solvent. Such a loop accounts for a low solvent level as well whether the nozzle tip is mis-aligned nozzle to the solvent pool.

Another method of controlling the level of solvent in cap fixture 216, illustrated in FIG. 8B, includes reducing the level of solvent from a desired level 804 to a level 816. The level can be reduced by pulling solvent to an external reservoir. Reducing the level of solvent to level 816 can be determined by a detector 818 positioned at level 816 that detects a meniscus. Detector 818 can be an ultrasonic detector manufactured by Cosense, Inc. of Hauppauge, N.Y. The amount of solvent removed can be measured, and, therefore, is known. Prior to another nozzle tip cleaning, the known amount of fluid can be metered and pumped back into cap fixture 216 to restore the level of solvent to level 804.

Additionally, the presence of bubbles in the solvent anywhere in the device is undesirable, including within cap fixture 216. An ultrasonic sensor 820 positioned within cap fixture 216 can be used to detect the presence of bubbles. If the bubble volume is larger than a selected value, then the wet cap system can be purged by removing the solvent and replaced with fresh solvent.

After the spray nozzle shifts aways from wetcap device 216 to funnel 214A, spray nozzle 206 can be programmed to be purged over funnel 214A at selected times and rates prior to the restart of the coating process.

A number of parameters influence the magnitude and consistency of the mass per pass of coating material applied by a spray nozzle and coating quality, in general. These parameters include the mass flow rate of gas and liquid feed to spray nozzle 206 shown in FIG. 2, the liquid/gas ratio fed to spray nozzle 206, the distance between the spray nozzle and a stent supported on a stent support assembly, the rotation rate of a stent support assembly, and the translation rate of spray nozzle 206. The liquid/gas ratio is critical since it determines the size of droplets produced by the spray nozzle. As the liquid/gas ratio increases, the size of the droplets increases. Device 200 allows adjustment of each of the parameters to obtain a desired mass per pass and coating quality.

In particular, it is important for the mass flow rate of liquid and gas to remain at selected levels throughout coating process so that the amount of coating material deposited per pass remains constant. As a result, the overall mass of coating material deposited on the stent is consistent and predictable from stent to stent.

In some embodiments, device 200 controls the flow of gas and liquid with a closed loop continuously monitored system. Device 200 can include integrated components for control of the mass flow rate of the liquid and gas delivered to spray nozzle 206. As discussed above, liquid coating material and gas are fed into spray nozzle 206. Liquid coating material is fed into port 212 through a hose or tubing (not shown) and gas is fed through hose 210.

Figure 9A:
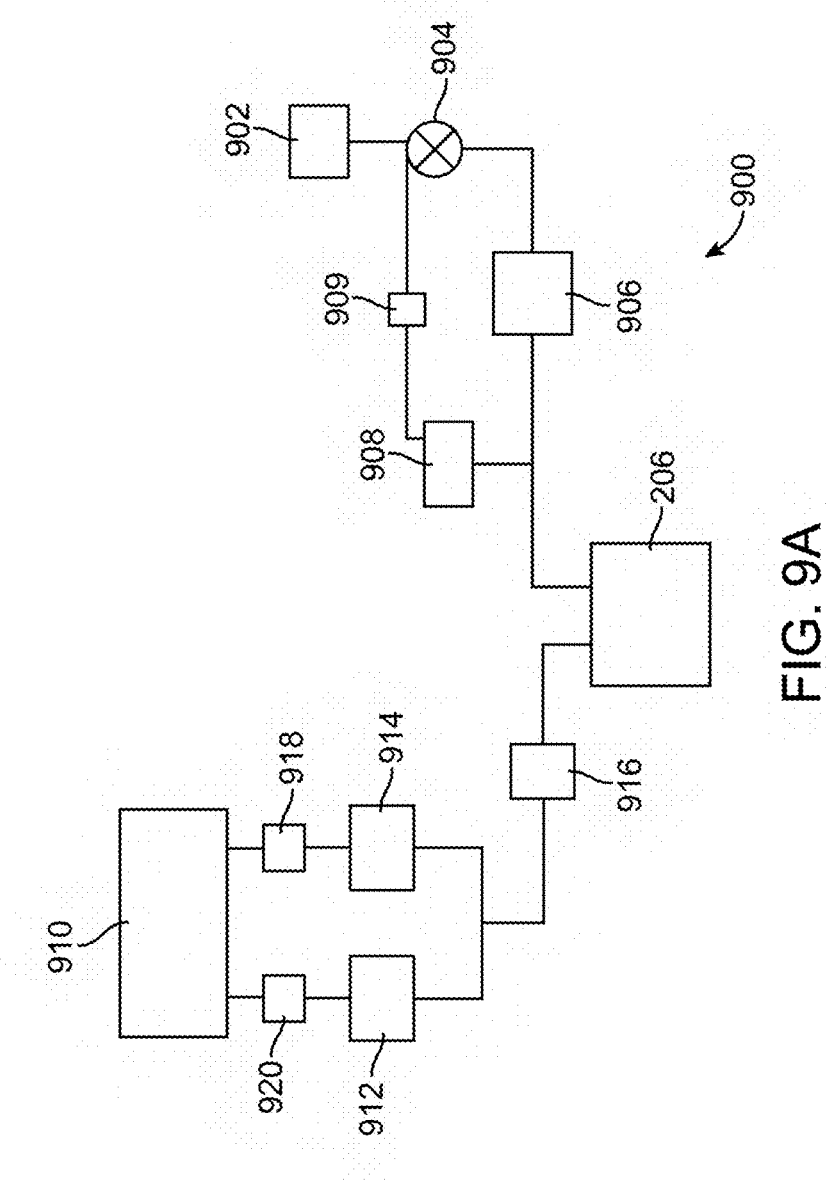
FIG. 9A depicts a schematic diagram of a system for controlling the liquid and gas flow delivered to a spray nozzle.
Figure 9B:
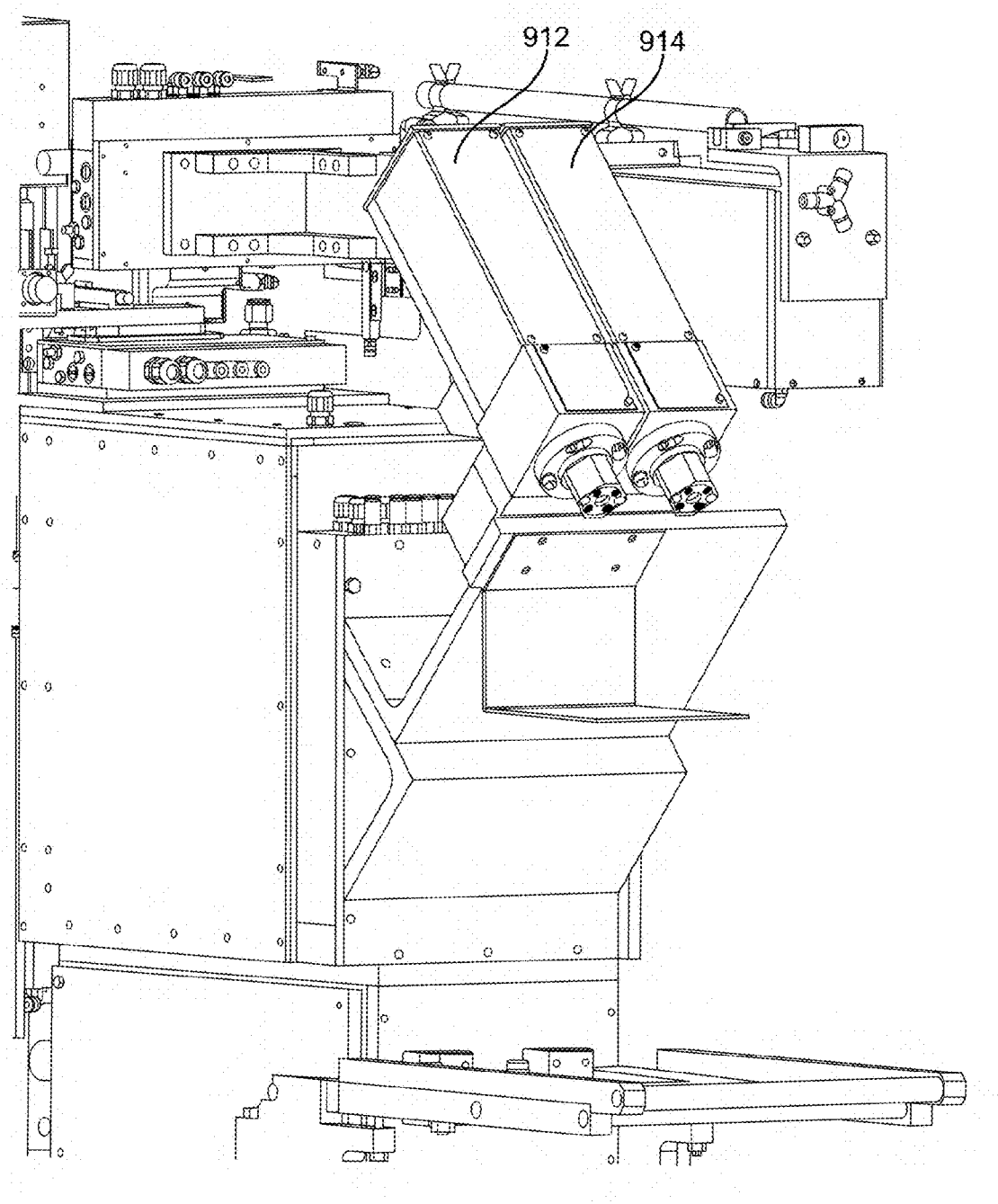
FIG. 9B depicts a view of the device in FIG. 1 showing metering pumps.

FIG. 9A depicts a schematic diagram of a system 900 of components for controlling the liquid and gas flow delivered to spray nozzle 206. The gas flow line of system 900 includes a gas source 902, pressure regulator 904, mass flow controller 906, and pressure transducer 908. Liquid coating material is delivered from a liquid source 910 by metering pumps 912 and 914 to spray nozzle 206. The liquid and gas meet at the tip of nozzle 206, and the liquid drop is broken up into smaller droplets by the gas (so-called atomization process). FIG. 9B depicts a close-up view of device 200 showing metering pumps 912 and 914 for the liquid coating material.

Mass flow controller 906 maintains a selected mass flow rate of gas and pressure transducer 908 monitors the gas pressure in the gas line to spray nozzle 206. Mass flow controller 906 monitors and controls the mass flow rate of gas passed through mass flow controller 906 to maintain the mass flow rate of gas delivered to spray nozzle 206. Mass flow controller 906 can compensate for an increase or decrease in mass flow rate of gas due to the pressure difference that occurs between valve 904 and the location in the gas line of mass flow controller 906. A decrease in mass flow rate can be caused, for example, by frictional losses. Mass flow controller 906 can be any suitable commercially available gas mass flow controller, for example, a thermal mass flow controller. An example of a commercially available mass flow controller is MC20A high flow mass controller from MKS Instruments, Inc. Mass flow controller 906 can include a valve which adjusts the flow rate based on detected changes in the flow rate of gas.

Pressure transducer 908 is positioned in the gas line between mass flow controller 906 and spray nozzle 206. Positive departures in the pressure can be caused by, for example, blockage of the nozzle by coating material or blockage due to kinked hoses. Negative departures in the pressure may be due to leaks, for example, resulting from loose fittings. Pressure transducer 908 monitors pressure in the gas line for changes in pressure and is in communication with valve 904 through a controller 909. A selected change in backpressure detected by pressure transducer 908 is compensated for through a control signal from controller 909 to pressure valve 904.

Metering pumps 912 and 914 deliver a selected flow rate of liquid to spray nozzle 206. Pumps 912 and 914 precisely meter liquid to spray nozzle 206. Pumps 912 and 914 act in tandem to allow precise metering and to enable continuous spraying. As one pump is dispensing the liquid to nozzle 206, the other pump is aspirating liquid from reservoir 910. The use of two pumps in tandem is an advantage over a single larger pump since the smaller the pump, the more accurate the dispensing of a small amount of liquid to the nozzle.

Additionally, as indicated above, the presence of bubbles in the liquid line is generally undesirable. The presence of bubbles tends to cause a negative departure from the desired mass of coating material deposited on the stent by spray nozzle 206. Bubbles in the pumps 912 and 914 also reduce the accuracy of the mass of liquid coating material dispensed by the pumps. Bubbles can be generated, for example, through the aspirating of pumps 912 and 914. The more volatile the solvent, the greater is the propensity of a pump to generate bubbles during aspirating. Bubble detectors can be positioned at any point along the liquid line as shown by bubble detectors 916, 918, and 920. Bubble detectors 916, 918, and 920 can monitor the volume of bubbles in the liquid coating material. If the detected volume is greater than a selected tolerance, a signal can be generated by a control system to communicate an alarm and/or take corrective action. Corrective action can include purging the liquid line, pumps, inspecting any leakage from the line, and/or reservoir of solvent.

Figure 10:
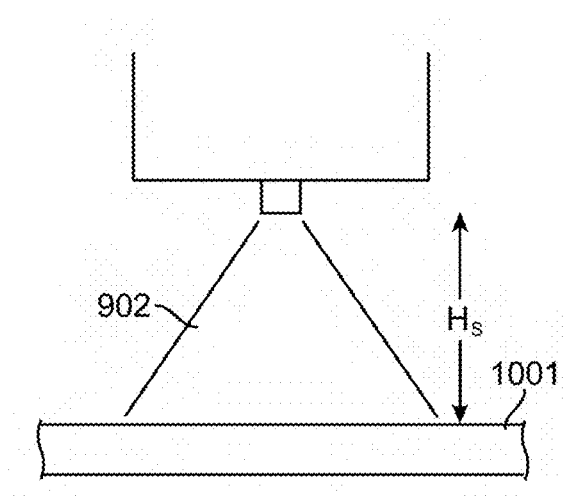
FIG. 10 depicts a schematic of a spray nozzle above a stent.

In some embodiments of device 200 shown in FIG. 2, a distance between either or both spraying nozzle 206 or drying nozzle 224 and a stent support assembly can be adjustable. Spraying nozzle 206 can be coupled to mounting bracket 220 via a screw that allows the distance between the nozzle and the stent support assembly to be varied. Drying nozzle 224 is mounted in a similar manner. Referring to FIG. 10, with respect to spraying, a height ($H_S$) above a stent 1001 is a process parameter that can be used to control the mass per mass deposited on stent 1001. The density and size of the droplets in a spray plume 902 varies with $H_S$. Therefore, $H_S$ influences the characteristics of a resultant coating. Furthermore, the distance between the drying nozzle 224 and a stent support assembly is an additional drying process parameter in addition to gas stream temperature and flow rate.

In further embodiments, either or both spray nozzle 206 or drying nozzle 224 are detachable from device 200. Spraying nozzle 206 is detachable from all connections with device 200. Spraying nozzle 206 can be releasably coupled to mounting bracket 220 by various types of mounting mechanisms known in the art, for example, dovetail connectors, butterfly connectors, nuts and bolts, etc. Drying nozzle 224 can also be releasably coupled in a similar manner to a mounting bracket (not shown). Gas feed hose 210 and liquid feed line that feeds liquid coating material into port 212 can also have quick-connect couplings to spray nozzle 206.

Such known connection mechanisms can be configured to allow the mounting and positioning of a nozzle in a repeatable manner, i.e., a nozzle can be placed in the same position each time it is mounted. The releasable connections allow spray nozzle 206 and drying nozzle 224 to be lifted out and inserted back into device 200 in to a designated position with respect to stent support assemblies 208 and 222.

A spray nozzle for coating a stent can be assembled and calibrated external to device 200. For example, a spray plume from the nozzle can be calibrated so that it has selected properties. The selected properties can include, but are not limited to, a selected flow distribution that corresponds to a liquid and gas flow rate into the nozzle. The flow distribution can include the velocity or density of droplets as a function of distance from the nozzle tip. The calibrated spray nozzle can then be mounted in spray device 200 such that a spray plume from the mounted nozzle has the selected properties.

The detachability and repeatability are particularly important when device 200 is used in an automated fashion. Additionally, detachability and repeatability allows rapid replacement of spray or dry nozzles with clean nozzles or nozzles more appropriate for different applications. Detachability of a spray nozzle for cleaning away from device 200 reduces idle time of device 200.

It is important for the drying process to be performed in a consistent manner for each layer and each stent. The same or similar processing conditions or parameters should exist for each layer of coating material applied for each stent. Drying process parameters can influence the molecular structure and morphology of a dried polymer and drug coating. Drug release parameters depend upon on molecular structure and morphology of a coating. Therefore, drug release parameters depend upon parameters of the drying process. For example, generally, the rate of a drying process is directly proportional to the resultant drug release rate of a resultant coating.

Since the temperature of a drying process is directly related to the rate of drying, it is important to control the drying temperature to obtain coating consistency. In general, the more consistent the temperature during the drying process from layer to layer and stent to stent, the more consistent the resultant coating in a given stent and from stent to stent.

The temperature of a warm gas stream that is used to dry a stent may be adjusted by controlling the heat supplied by electrical heater 230, depicted in FIG. 2. Temperature sensor 506 shown in FIGS. 5A-B is positioned adjacent to a stent supported by a stent support assembly to measure the drying temperature of the applied coating. Temperature sensor 506 is positioned as close as possible to stent without significantly disrupting the flow of heated fluid past the stent. In one embodiment, there is no or substantially no offset or difference in temperature between the drying temperature of the coating on the stent and the temperature measured by sensor 506. In other embodiments, sensor 506 is positioned far enough away so that there is an offset in the measured temperature and the drying temperature. Such an offset can be taken into account in a control system described below. Temperature sensor 506 can be a thermistor, thermocouple, or any other temperature measuring device.

Temperature sensor 506 measures the drying temperature to gather feedback ($T_F$) for controlling the drying temperature of a stent mounted on a stent support assembly. Sensor 506 is coupled to a control system by a sensor wire. Any suitable control system, such as a closed loop system, can be used for maintaining the drying temperature of the coating at a desired temperature ($T_D$). A temperature, $T_F$, measured by sensor 506 is transmitted to the control system. The control system compares $T_F$ to $T_D$ and then transmits a signal to electrical heater 230. The signal carries instructions to heater 230 to adjust the temperature of the warm gas stream supplied from drying nozzle 224 if the difference in temperature is larger than a selected tolerance. In some embodiments, the desired temperature $T_D$ can be a function of drying time or coating thickness.

As described above, device 200 includes stent support assemblies 208 and 222. In general, a stent can be supported on a mandrel or rod that supports the stent along its length by positioning the stent over the mandrel. A stent can also be supported at its ends with supports having a variety of geometries, such as supports with tapered or untapered ends. Thus, the present invention is not limited to the stent supports disclosed in the present application.

Figure 11A:
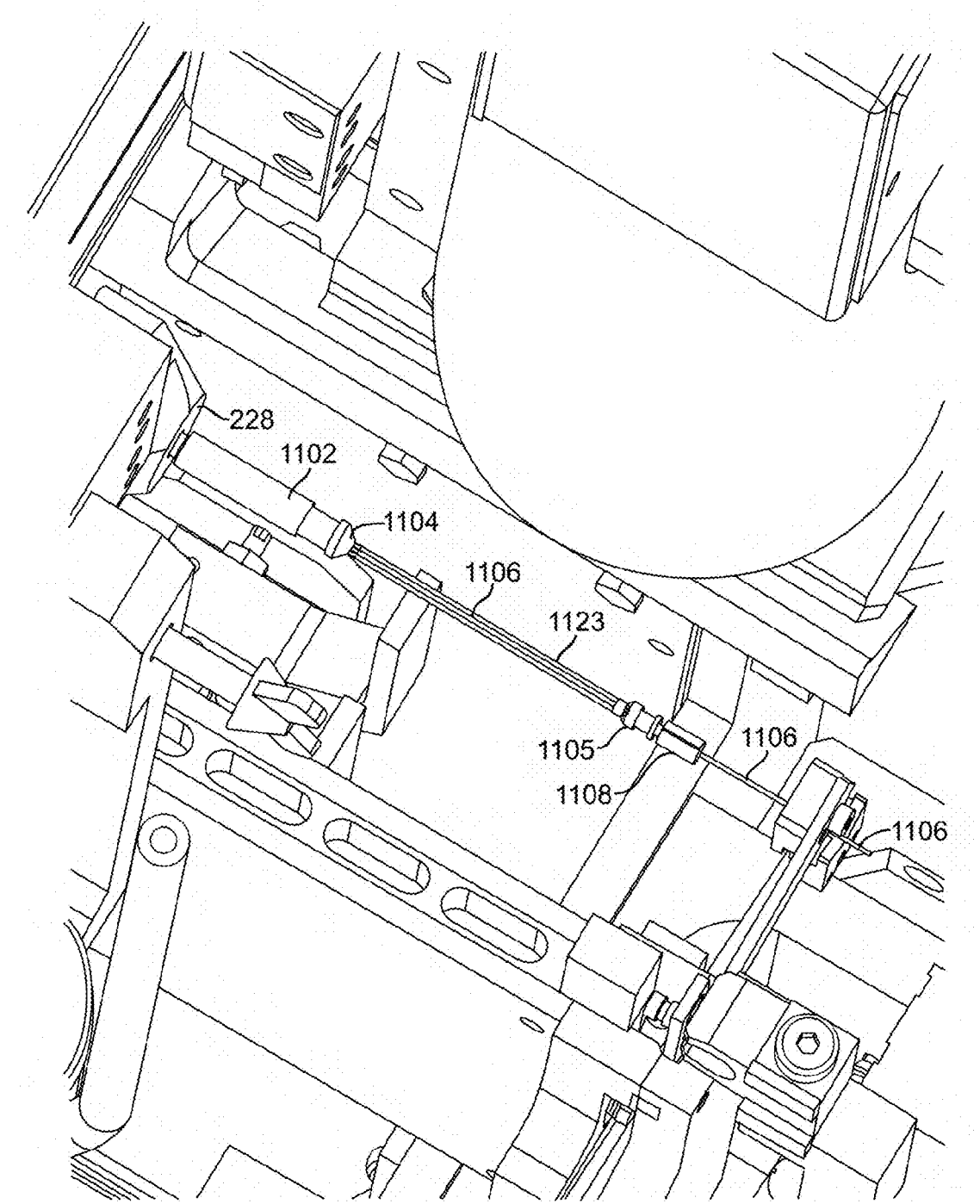
FIGS. 11A-C depict close-up views of a stent support assembly for supporting a stent during a spraying and drying process.
Figure 11B:
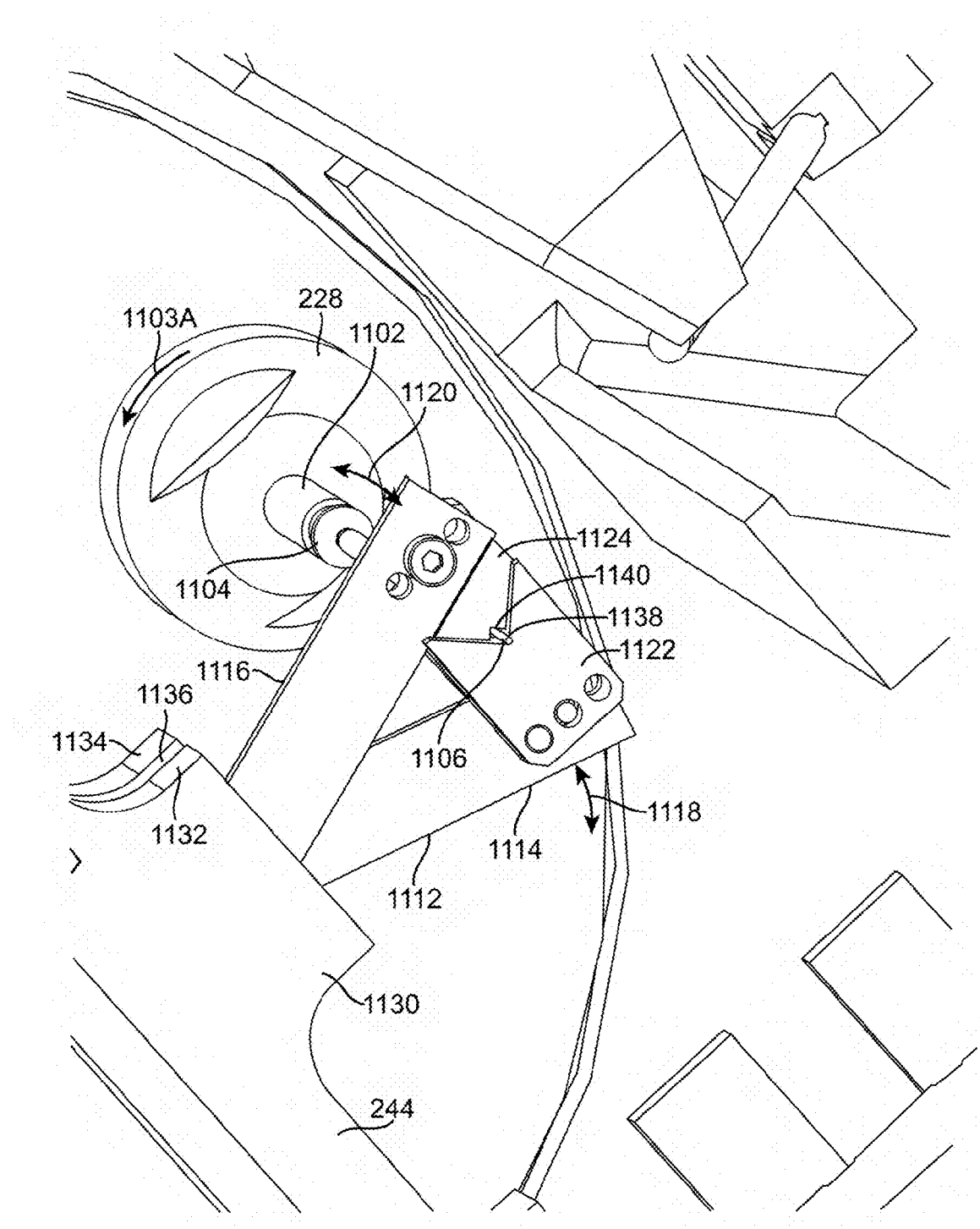
Figure 11C:
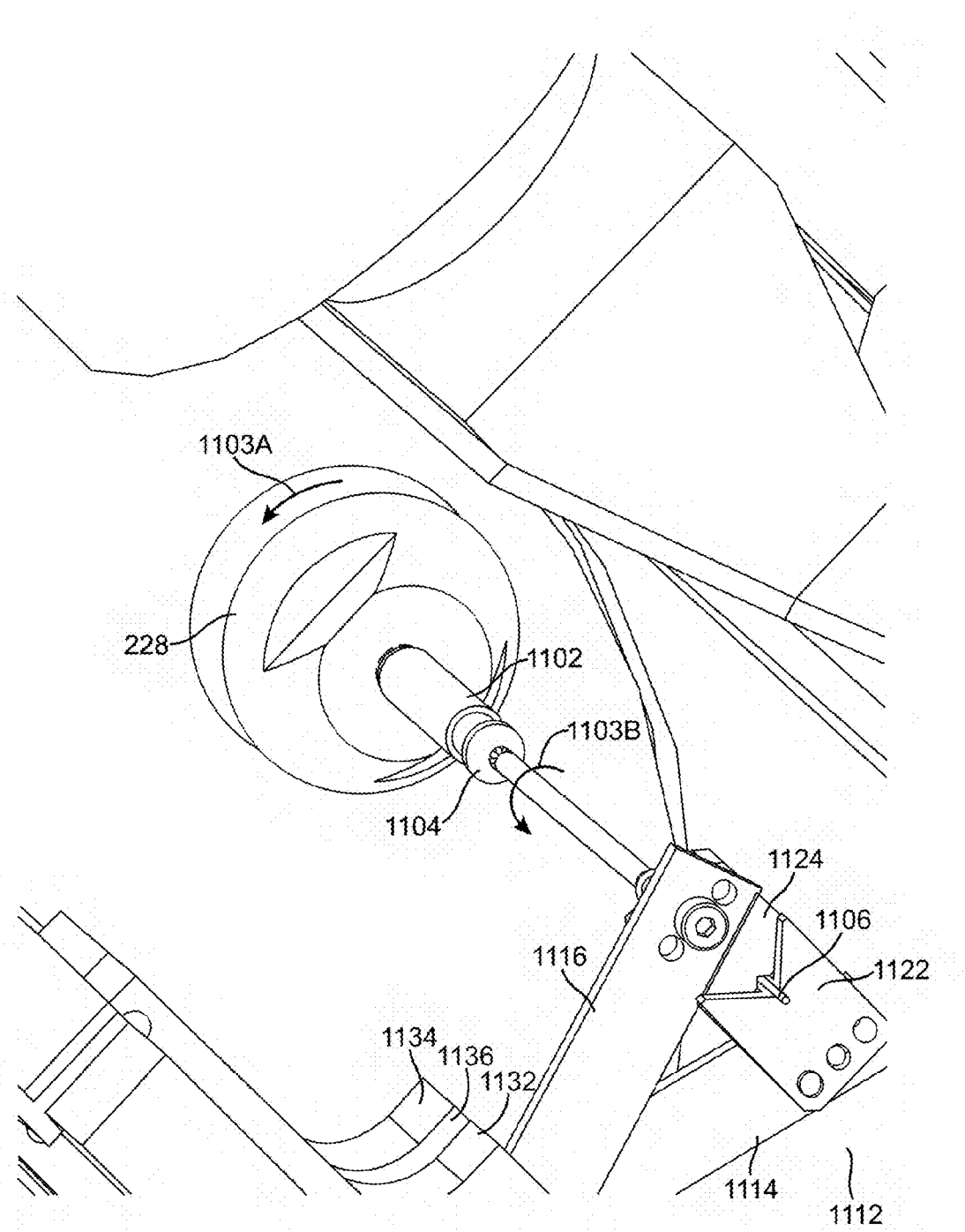

FIGS. 11A-C depict close-up views of a stent support assembly for supporting a stent during a spraying and drying process. The stent support assembly has a distal portion or shank 1102. A portion of shank 1102 is secured within a cylindrical hole in spindle or end cap 228 which rotates, as shown by an arrow 1103A in FIG. 11B in FIG. 11C, to rotate the stent support assembly, as shown by an arrow 1103B, during coating and drying of a stent mounted on the stent support assembly. The stent support assembly further includes a mandrel cone 1104 for supporting a distal end of a stent and a mandrel cone 1105 for supporting a proximal end of the stent. As shown in FIG. 11A, a core wire 1106 extends from the tip of mandrel cone 1104 and through a collet 1108 with a mandrel cone space 1105. Mandrel cones 1104 and 1105 can have a roughened surface to absorb excess coating material. A stent 1123 is shown supported by mandrel cones 1104 and 1105 over core wire 1106.

Core wire 1106 has a diameter less than a stent. For example, core wire 1106 has a diameter between about 0.010" and 0.030". Core wire 1106 can be made of a metallic material such as Nitonol wire which can provide good dimensional stability and rigidity.

As shown in FIG. 11B, core wire 1106 is supported at a proximal end by a tailstock support 1112. Tailstock support 1112 is a scissor-like mechanism with two movable flat extension arms 1114 and 1116 that can open as shown by arrows 1118 and 1120, respectively. Flat extension arms 1122 and 1124 with opposing wedge- or v-shaped cut-out sections are coupled to distal ends of movable extended arms 1114 and 1116, respectively. Arms 1114 and 1116 are coupled to baffle 244 by a support fixture 1130 that is coupled to baffle 244. Support fixture 1130 is composed of two end plates 1132 (outer) and 1134 (inner) that are used to house and support flat extension arms 1114 and 1116. Proximal ends of extension arms 1114 and 1116 (one from drying zone 204 and one from spray zone 202) are connected to two bars (one at an upper location and one at a lower location) which are linked to an air cylinder to pull them up or down to close or open the tailstock support.

The proximal end of core wire 1106 is clamped at the apices 1138 and 1140 of the opposing wedge-shaped cut-out sections of plates 1122 and 1124. Therefore, the stent support assembly can be rotated with little or no deviation of core wire 1106 from the rotational axis. Tailstock support 1112 prevents any excessive movement at the distal end of core wire 1106 as it rotates about its axis and during rotation of rotatable drum 240.

Figure 11D:
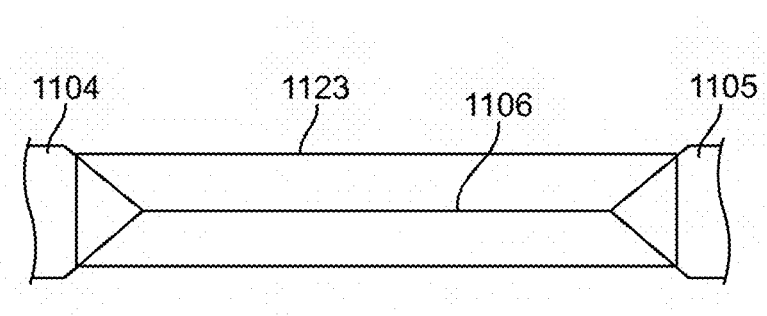
FIGS. 11D-E depicts an axial cross-section of a stents mounted on mandrels.

As shown in FIG. 11D, a stent 1123 can be mounted between mandrel cones 1104 and 1105 to obtain 1:1 rotation between stent 1123 and mandrel cones 1104 and 1105. The gap between the end rings of stent 1123 and mandrel cones 1104 and 1105 can be adjusted to provide an optimal contact force to assure that mandrel cones 1104 and 1105 and stent 1123 have the same or substantially the same axes of rotation.

However, the exerted force should not compress stent 1123 so as to distort the body of stent 1123. Over or under application of support force can lead to problems such as stent 1123 resting too loosely on the stent support assembly, stent 1123 bending, opposing ends of stent 1123 flaring on mandrel cones 1104 and 1105, and increased contact between stent 1123 and mandrel cones 1104 and 1105, all of which can lead to coating defects.

Figure 11E:
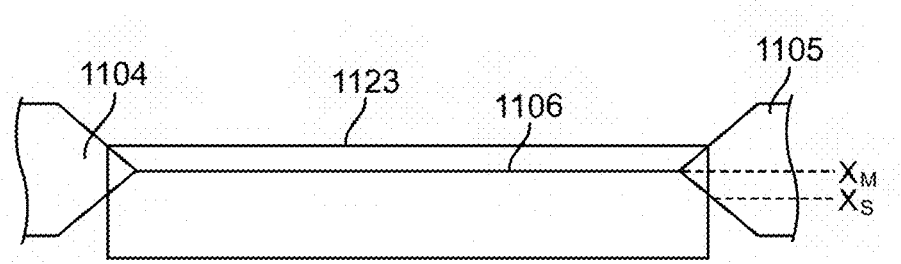

In other embodiments, a stent does not have a 1:1 rotation with supporting end elements such as mandrel cones 1104 and 1105. As shown in FIG. 11E, stent 1123 can be mounted on mandrel cones 1104 and 1105 so that stent 1123 and mandrel cones 1104 and 1105 have a different axis of rotation. Mandrel cones 1104 and 1105 have an axis of rotation $x_M$ and stent 1123 has an axis of rotation $x_S$ longitudinally through its center. Thus, the contact points or area between mandrel cones 1104 and 1105 and stent 1123 continuously change.

Another aspect of the present invention relates to reducing or eliminating coating defects that can result from stent contact with supports, such as mandrels, during coating. While some coating defects can be minimized by adjusting the coating parameters, other defects occur due to the nature of the interface between the stent and the apparatus on which the stent is supported during the coating process. Surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the influence of the interface between the stent and the supporting apparatus during the coating process to reduce or eliminate coating defects. As indicated above, the interface or contact points between a stent support and the stent can lead to defects. This is particularly the case where the support and the stent have 1:1 rotation, and thus, do not move relative to one another during the coating process. The lack of relative movement can lead to stationary contact points caused by the stent adhering to the support at a point of contact.

The contact area between a support and stent can be minimized when the support has a different axis of rotation than the stent. As described above, the ends of a stent can be supported loosely over tapered ends such as cones. Thus, as the mandrel rotates, the contact points continuously change. Even in this approach, the stent can stick to the support members, resulting in stationary contact points.

Figure 12A:
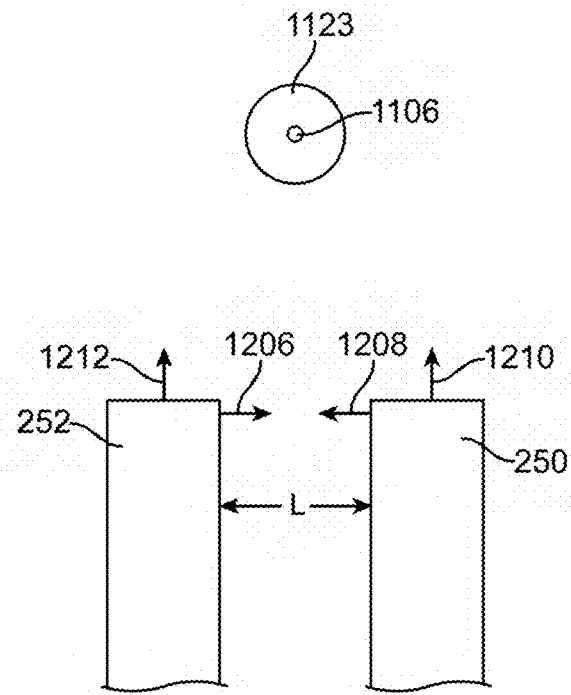
FIGS. 12A-C depicts a close-up view of the stent grippers from FIG. 1.

Embodiments of the present invention include shifting or changing the contact points of a stent during a coating process to minimize the coating defects at the contact points. As shown in FIG. 2, stent gripper plates 250 and 252 provide a mechanism to steadily hold the stent on stent support assembly 222 to enable the stent support assembly to move the contact points of the stent with the stent support assembly. FIG. 12A depicts a close-up view of stent gripper plates 250 and 252 from FIG. 2 positioned below stent 1123 disposed over core wire 1106. Stent gripper plates 250 and 252 are disposed at a distance L from one another, the distance L being greater than the outside diameter of a stent that is being coated. Stent gripper plates 250 and 252 can be shifted toward each other as shown by arrows 1206 and 1208 and upwards towards a stent support assembly positioned above stent grippers 250 and 252.

Figure 12B:
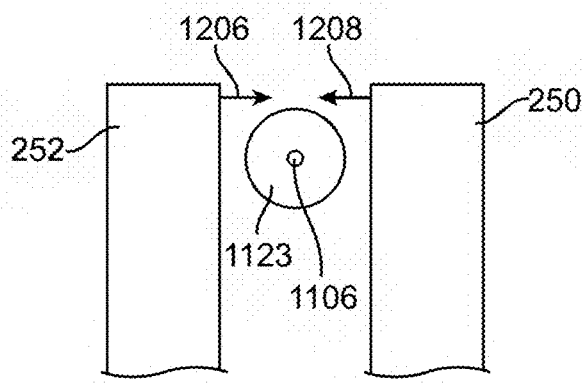
Figure 12C:
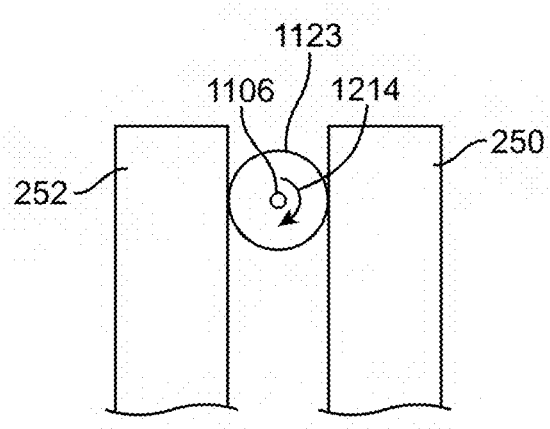

Upon drying of a stent, stent gripper plates 250 and 252 are first shifted upwards to the stent support assembly so that stent 1123 is between stent gripper plates 250 and 252, as depicted in FIG. 12B. The rotation of the stent support assembly is stopped so that stent 1123 is not rotating. Stent gripper plates 250 and 252 then move towards one another as shown by arrows 1206 and 1208. As depicted in FIG. 12C, stent grippers 250 and 252 move close to each other to a predetermined gap which will hold stent 1123 stationary while stent support assembly rotates with respect to stent 1123, as shown by an arrow 1214. The stent support assembly can be rotated or clocked just enough to move any contact points between stent 1123 and any part of the stent support assembly, for example, less than 5°. Alternatively, the stent support assembly can be rotated greater than 5°, 10°, 30°, 60°, 90°, 270°, or greater than 360°. In addition, the stent support assembly can be rotated clockwise or counter-clockwise. The rotating or clocking can be unidirectional or bi-directional. For example, the mandrel can be clocked back and forth one or more times.

There are alternative methods of moving contact points or breaking stationary contact points between a stent and a support. In one embodiment, a stent support can be vibrated to break stationary contact points. For example, an ultrasonic device such as a transducer can be used to vibrate a stent support or stent grippers. In another embodiment, a stream or puff of air can be directed at a stent mounted on a support to disturb stationary contact points.

Stent and Coating Materials

A non-polymer substrate for an implantable medical device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In accordance with one embodiment, the coating composition can include a solvent and a polymer dissolved in the solvent and optionally a wetting fluid. The composition can also include active agents, radiopaque elements, or radioactive isotopes. Representative examples of polymers that may be used as a substrate of a stent or coating for a stent, or more generally, implantable medical devices include, but are not limited to, poly(N-acetylglucosamine) (Chitin), Chitosan, poly(-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D, L-lactide), poly(L-lactide-co-D,L-lactide), poly (caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa., or Kynar 2750, available from Arkema), ethylene-vinyl acetate copolymers, poly(vinyl acetate), styrene-isobutylene-styrene triblock copolymers, and polyethylene glycol.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

A "wetting" of a fluid is measured by the fluid's capillary permeation. Capillary permeation is the movement of a fluid on a solid substrate driven by interfacial energetics. Capillary permeation is quantified by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of the wetting fluid include, but are not limited to, tetrahydrofuran (THF), dimethylformamide (DMF), 1-butanol, n-butyl acetate, dimethylacetamide (DMAC), and mixtures and combinations thereof.

Examples of radiopaque elements include, but are not limited to, gold, tantalum, and platinum. An example of a radioactive isotope is $p^{32}$. Sufficient amounts of such substances may be dispersed in the composition such that the substances are not present in the composition as agglomerates or flocs.

Active Agents

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, anti-platelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such anti-platelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Tables 1a-d and 2a-d include spray-coating results for a coated stent using an exemplary spray coating device 200. Tables 1a-d provide coating results for an exemplary device referred to as machine 1 and Tables 2a-d provide coating results for an exemplary device referred to as machine 2. Each table represents data for a set of stents. Tables 1a-b and 2a-b are coating results of a poly(butyl methacrylate) (PBMA) primer and 1c-d and 2c-d are coating results for the poly(vinylidene fluoride-co-hexafluoropropene) (PVDF-HFP) drug coating over the primer layer. The coating weight is in μg. The relative standard deviation (RSD) is used to gauge the applied coating weight consistency per spray repetition.

TABLE 1a

Spraying results for 8 mm stent for machine 1.
Machine 1 (8 mm Medium)

| Back Sprayer | Actual Coating Weight | Actual Mass Per Pass |
|---|---|---|
| Average | 273.2 | 4.6 |
| STDev | 6.6 | 0.1 |
| Minimum | 262 | 4.4 |
| Maximum | 290 | 4.8 |
| RSD | 2.4% | 2.4% |
| Coating Integrity Yield | | 100% |

TABLE 1b

Spraying results for 8 mm stent for machine 1.
Machine 1 (8 mm Medium)

| Back Sprayer | Actual Coating Weight | Actual Mass Per Pass |
|---|---|---|
| Average | 272.7 | 4.5 |
| STDev | 7.2 | 0.1 |
| Minimum | 260 | 4.3 |
| Maximum | 288 | 4.8 |
| RSD | 2.6% | 2.6% |
| Coating Integrity Yield | | 95.83% |

TABLE 1c

Spraying results for 8 mm stent for machine 1.
Machine 1 (8 mm Medium)

| Back Sprayer | Actual Coating Weight | Actual Mass Per Pass |
|---|---|---|
| Average | 1132.9 | 18.9 |
| STDev | 18.7 | 0.3 |
| Minimum | 1082 | 18.0 |
| Maximum | 1166 | 19.4 |
| RSD | 1.7% | 1.7% |
| Coating Integrity Yield | | 90.63% |

TABLE 1d

Spraying results for 8 mm stent for machine 1.
Machine 1 (8 mm Medium)

| Back Sprayer | Actual Coating Weight | Actual Mass Per Pass |
|---|---|---|
| Average | 1116.3 | 18.6 |
| STDev | 24.3 | 0.4 |

TABLE 1d-continued

Spraying results for 8 mm stent for machine 1.
Machine 1 (8 mm Medium)

| Back Sprayer | Actual Coating Weight | Actual Mass Per Pass |
|---|---|---|
| Minimum | 1076 | 17.9 |
| Maximum | 1162 | 19.4 |
| RSD | 2.2% | 2.2% |
| Coating Integrity Yield | | 100.00% |

TABLE 2a

Spraying results for 8 mm stent for machine 2.
Machine 2 (8 mm Medium)

| Back Sprayer | Actual Coating Weight | Actual Mass Per Pass |
|---|---|---|
| Average | 275.2 | 4.59 |
| STDev | 4.9 | 0.08 |
| Minimum | 263.0 | 4.38 |
| Maximum | 284.0 | 4.73 |
| RSD | 1.8% | 1.8% |
| Coating Integrity Yield | | 96.15% |

TABLE 2b

Spraying results for 8 mm stent for machine 2.
Machine 2 (8 mm Medium)

| Back Sprayer | Actual Coating Weight | Actual Mass Per Pass |
|---|---|---|
| Average | 273.2 | 4.6 |
| STDev | 5.3 | 0.1 |
| Minimum | 261 | 4.35 |
| Maximum | 284 | 4.73 |
| RSD | 1.9% | 1.9% |
| Coating Integrity Yield | | 96.15% |

TABLE 2c

Spraying results for 8 mm stent for machine 2.
Machine 2 (8 mm Medium)

| Back Sprayer | Actual Coating Weight | Actual Mass Per Pass |
|---|---|---|
| Average | 1113.7 | 18.56 |
| STDev | 23.9 | 0.40 |
| Minimum | 1082.0 | 18.03 |
| Maximum | 1167.0 | 19.45 |
| RSD | 2.1% | 2.1% |
| Coating Integrity Yield | | 100.00% |

TABLE 2d

Spraying results for 8 mm stent for machine 2.
Machine 2 (8 mm Medium)

| Back Sprayer | Actual Coating Weight | Actual Mass Per Pass |
|---|---|---|
| Average | 1098.0 | 18.3 |
| STDev | 17.2 | 0.3 |
| Minimum | 1071 | 17.85 |
| Maximum | 1133 | 18.88 |
| RSD | 1.6% | 1.6% |
| Coating Integrity Yield | | 96.43% |

Tables 3a-b include spraying and drying parameters used to obtain the above coating results. Table 3a provides examples showing the spraying process parameters for applying primer and drug coating. Table 3b shows an example of some common process parameters used in applying the primer and drug coating.

TABLE 3a

Coating parameters used in coating device.

| Parameter Description | Primer Coat | Drug coat polymer |
|---|---|---|
| IVEK Pump rate, ml/hr | 5 | 7.5 |
| Atomization air flow, LPM | 12 | 12 |
| Drying gas flow, LPM | 110 | 110 |
| Number of passes | 15 | 40 |
| # of spray passes per dry cycle | 3 | 3 |

TABLE 3b

Coating parameters used in coating device.

| Parameter Description | Parameter Value |
|---|---|
| Spindle Rotation Speed, rpm | 150 |
| Spray translation speed, mm/s | 16 |
| Drying Time, second | 10 |
| Drying Temp, ° C. | 45 |
| Nozzle Start Position, mm | 10 |
| Nozzle End Position, mm | 10 |

Figure 13:
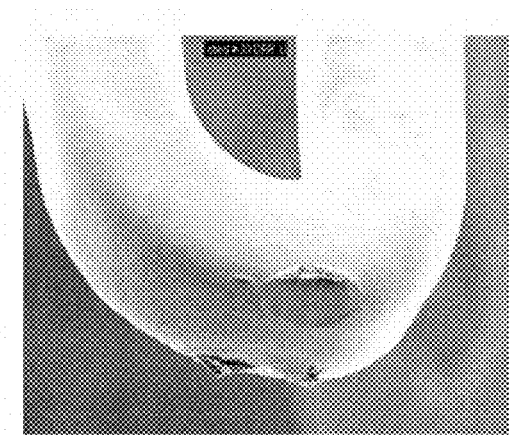
FIGS. 13-17 depict Scanning Electron Microscope images of a coated stent.
Figure 14:
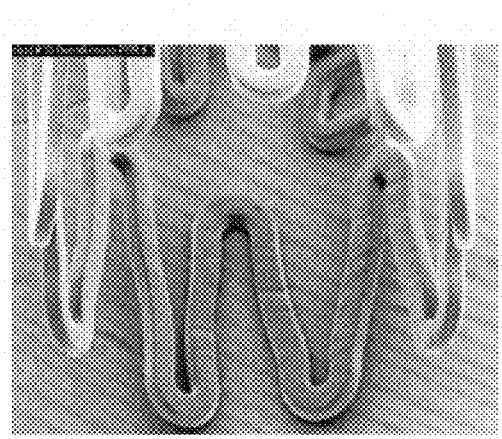
Figure 15:
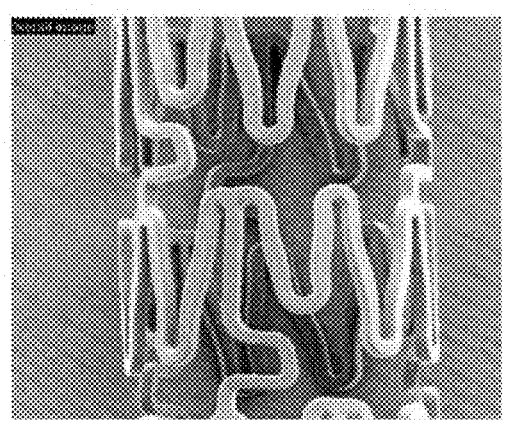
Figure 16:
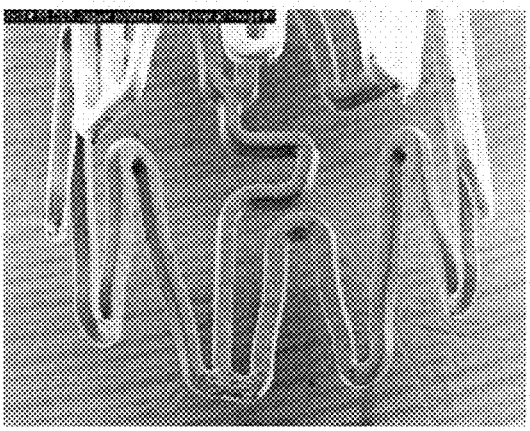
Figure 17:

FIGS. 13-17 are Scanning Electron Microscope images of a stent coated with an exemplary coating device 200. As above, the stent was coated with PBMA primer and PVDF-HFP. FIG. 13 depicts the U-crown of the coated stent. FIG. 14 depicts the proximal end of the coated stent. FIG. 15 depicts the overall coating quality of the coated stent. FIG. 16 depicts the distal end of the coated stent. FIG. 17 depicts a close-up view (400X high magnification) of the end ring.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A support assembly for supporting a stent during coating comprising:
   a first support element coupled to a rotatable spindle;
   a support wire, wherein a proximal end segment of the support wire extends from and is coupled to the first support element; and
   a clamping device supporting a distal end segment of the support wire, wherein the proximal end segment and the distal end segment of the of the support wire are positioned so that the support wire rotates concentrically with the first support element when the first support element is rotated by the rotatable spindle, and wherein the support wire rotates relative to the clamping device wherein the clamping device comprises arms that are movably coupled to each other such that the support wire is secured by the arms when the arms move toward each other.

2. The support assembly of claim 1, wherein the clamping device comprises arms that are movably coupled to each other such that the support wire is secured by the arms when the arms rotate inward move toward each other.

3. The support assembly of claim 2, wherein the arms each include a cut-out section, the cut-out sections configured to receive the support wire when the arms move toward each other.

4. The support assembly of claim 1, wherein a portion of the first support element is configured to support a first end of a stent.

5. The support assembly of claim 4, further comprising a second support element coupled to the support wire at a location between the first support element and the clamping device, wherein a portion of the second support element is configured to support a second end of the stent.

6. The support assembly of claim 5, wherein the portion of the first support element is a first cone configured to support the first end of the stent, and the portion of the second support element is a second cone configured to support the second end of the stent.

7. The support assembly of claim 1, wherein the first support element is movable into and out of the rotatable spindle.

8. The support assembly of claim 6, wherein the support wire is movable into and out of the clamping device.

* * * * *